US008712505B2

(12) United States Patent
Ishikawa et al.

(10) Patent No.: US 8,712,505 B2
(45) Date of Patent: Apr. 29, 2014

(54) AUTOMATED MACULAR PATHOLOGY DIAGNOSIS IN THREE-DIMENSIONAL (3D) SPECTRAL DOMAIN OPTICAL COHERENCE TOMOGRAPHY (SD-OCT) IMAGES

(75) Inventors: Hiroshi Ishikawa, Allison Park, PA (US); Gadi Wollstein, Pittsburgh, PA (US); Joel S. Schuman, Pittsburgh, PA (US); Yu-Ying Liu, Atlanta, GA (US); James M. Rehg, Atlanta, GA (US); Mei Chen, Pittsburgh, PA (US)

(73) Assignee: University of Pittsburgh-of the Commonwealth System of Higher Education, Pittsburgh, PA (US)

( * ) Notice: Subject to any disclaimer, the term of this patent is extended or adjusted under 35 U.S.C. 154(b) by 107 days.

(21) Appl. No.: 13/294,601

(22) Filed: Nov. 11, 2011

(65) Prior Publication Data

US 2012/0184845 A1 Jul. 19, 2012

Related U.S. Application Data

(60) Provisional application No. 61/412,695, filed on Nov. 11, 2010.

(51) Int. Cl.
*A61B 8/00* (2006.01)
*A61B 6/00* (2006.01)
*A61B 3/14* (2006.01)
*A61B 3/00* (2006.01)

(52) U.S. Cl.
USPC ........... 600/476; 351/206; 351/246; 600/452; 128/922

(58) Field of Classification Search
USPC ............ 600/437; 382/133; 351/246; 128/922
See application file for complete search history.

(56) References Cited

U.S. PATENT DOCUMENTS

| 7,992,999 | B2 * | 8/2011 | Xu et al. ...................... 351/206 |
| 7,997,729 | B2 * | 8/2011 | Mclean et al. ................ 351/206 |
| 8,355,554 | B2 * | 1/2013 | Ma et al. ...................... 382/131 |
| 2011/0280457 | A1 * | 11/2011 | Nielsen et al. ................ 382/131 |

OTHER PUBLICATIONS

Novotny, Adman, et al., "Texture Analysis of Nerve Fibre Layer in Retinal Images Via Local Binary Pattern and Gaussian Markov Random Fields". Analysis of Biomedical Signals and Images; (Jun. 2010) 20: 308-315.*
Zhang, Wenchao et al. "Local Gabor Binary Pattern Histogram Sequence (LGBPHS): A Novel Non-Statistical Model for Face Representation and Recognition". Proceedings of the Tenth IEEE International Conference on Computer Vision. (2005).*

* cited by examiner

*Primary Examiner* — Long V. Le
*Assistant Examiner* — Helene Bor
(74) *Attorney, Agent, or Firm* — Kegler Brown Hill & Ritter; James J. Pingor

(57) ABSTRACT

Systems and methods of analyzing an optical coherence tomography image of a retina are discussed. A 2-dimensional slice of the image can be aligned to produce an approximately horizontal image of the retina and an edge map based at least in part on the aligned slice. Also, at least one global representation can be determined based on a (multi-scale) spatial division, such as multi-scale spatial pyramid, on the slice and/or edge map. Creating the local features is based on the specified cell structure of the global representation. The local features can be constructed based on local binary pattern (LBP)-based features. Additionally, a slice can be categorized into one or more categories via one or more classifiers (e.g., support vector machines). Each category can be associated with at least one ocular pathology, and classifying can be based on the constructed global descriptors, which can include the LBP-based local descriptors.

17 Claims, 18 Drawing Sheets

AUTOMATED MACULAR PATHOLOGY DIAGNOSIS IN THREE-DIMENSIONAL (3D) SPECTRAL DOMAIN OPTICAL COHERENCE TOMOGRAPHY (SD-OCT) IMAGES

CROSS-REFERENCE TO RELATED APPLICATIONS

This application claims the benefit of U.S. Provisional Patent application Ser. No. 61/412,695 entitled "AUTOMATED MACULAR PATHOLOGY DIAGNOSIS IN THREE-DIMENSIONAL (3D) SPECTRAL DOMAIN OPTICAL COHERENCE TOMOGRAPHY (SD-OCT) IMAGES" and filed Nov. 11, 2010. The entirety of the above-noted application is incorporated by reference herein.

BACKGROUND

Spectral-domain optical coherence tomography (SD-OCT) is a non-contact, non-invasive three-dimensional (3D) imaging technique, which performs optical sectioning at micron resolution. OCT was commercially introduced to ophthalmology in 1996, and is widely used in ophthalmology for identifying the presence of various ocular pathologies and their progression. This technology measures the optical back scattering of the tissues, making it possible to visualize intraocular structures such as the retina and the optic nerve head. The ability to visualize the internal structure of the retina makes it possible to diagnose ocular diseases, such as glaucoma and macular hole, objectively and quantitatively.

Although OCT imaging technology continues to evolve, technology for automated OCT image analysis and interpretation has not kept pace. With OCT data being generated in increasingly larger amounts and captured at increasingly higher sampling rates, there is a strong need for computer assisted analysis to support disease diagnosis and tracking. This need is amplified by the fact that an ophthalmologist making a diagnosis under standard clinical conditions does not have assistance of a specialist in interpreting OCT data. This is in contrast to other medical imaging situations, where a radiologist is usually available.

The macula is located at the center of the retina and is responsible for highly-sensitive, accurate vision. Acute maculopathy can cause the loss of central, sharp vision and even lead to blindness. For example, diabetic retinopathy, one of the leading causes of blindness worldwide, is often associated with macular edema (ME). According to a study conducted in 2004, among an estimated 10.2 million US adults aged 40 and older known to have diabetes mellitus, the estimated prevalence rate for retinopathy was 40.3%. Another type of maculopathy, called age-related macular degeneration (AMD), is the leading cause of visual loss among elderly persons. One study reported that 30% of individuals aged 75 and older have some form of AMD. Another disease that can lead to blindness is called macular hole (MH), which is less common than ME and AMD. The overall prevalence is approximately 3.3 cases in 1000 in those persons older than 55 years. As the size of the elderly population increases in the US and many developed countries, the prevalence of maculopathy has increasingly significant social and economic impact. Thus, the diagnosis and screening of macular disease is important to public health.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises a method of analyzing an optical coherence tomography (OCT) image of a retina. The method can include the acts of aligning a 2-dimensional (2D) slice of the OCT image to produce an approximately horizontal image of the retina and constructing an edge map based at least in part on the aligned 2D slice. Also, the method can include the step of determining at least one global representation based at least in part on the 2D slice or the edge map and the step of creating the local features, which include at least in part the local binary pattern (LBP)-based features, based at least in part on the at least one global representation. Additionally, the method can include the act of classifying the 2D slice into one or more categories via one or more learned classifiers, such as support vector machines (SVMs). Each category can be associated with at least one ocular pathology, wherein the classifying can be based at least in part on the at least one LBP-based features.

In another aspect, the subject innovation, can comprise a system that facilitates automated diagnosis of diseases. The system can include an alignment component that can align a 2-dimensional (2D) slice of an optical coherence tomography (OCT) image to produce an aligned slice. The system can also include a feature construction component that can determine at least one global representation and at least one local descriptor based on the aligned image. Additionally, there can be a classification component that can comprise one or more classifiers. Each classifier can classify the aligned image into one of a plurality of categories associated with at least one ocular pathology.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
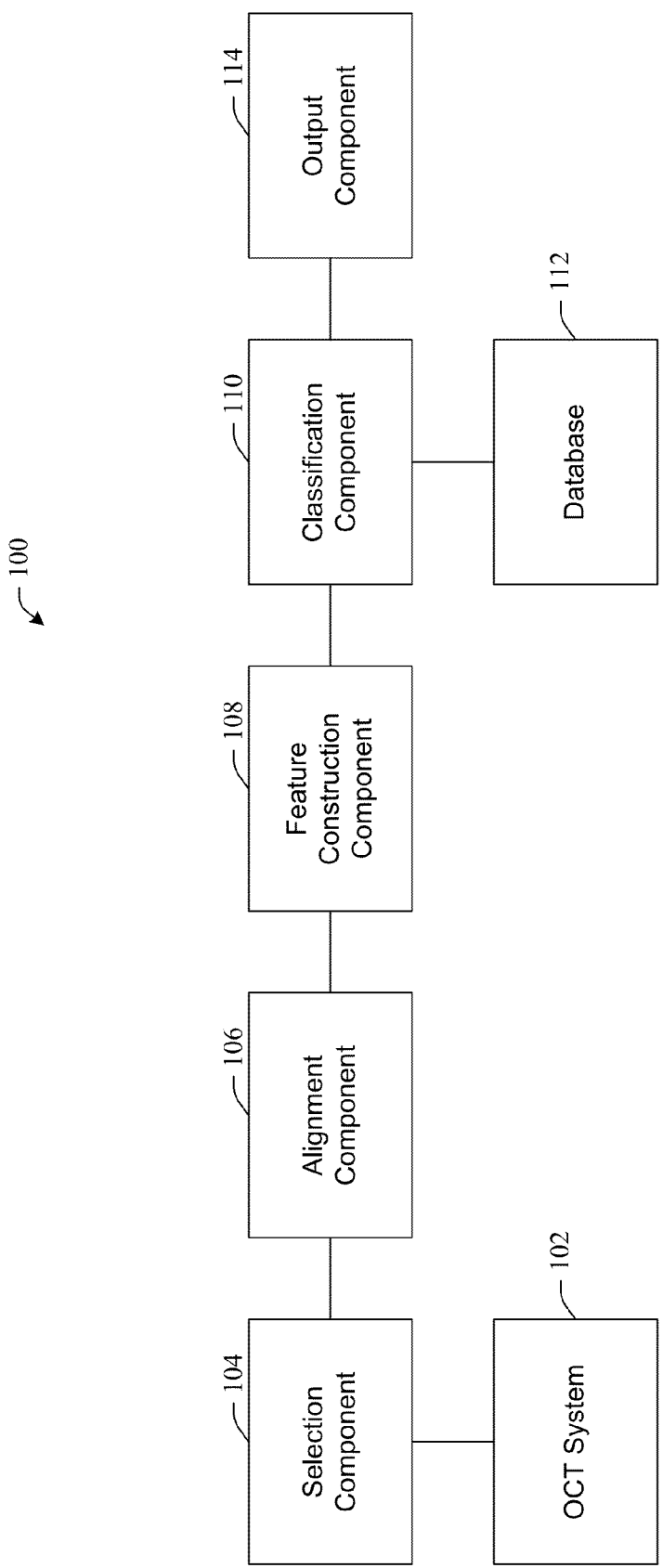
FIG. 1 illustrates an example system capable of determining the presence or absence of one or more retinal pathologies in accordance with aspects of the subject innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term to "infer" or "inference" refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

Systems and methods of the subject innovation facilitate computer-aided diagnosis of retinal pathologies. Techniques described herein can be applied to optical coherence tomography (OCT) images to determine the presence or absence of one or more retinal pathologies, or to sub-categorize conditions. For example, various embodiments of the subject innovation provide automated techniques that can identify the normal macula and macular pathologies (e.g., macular hole (MH), macular edema (ME), and age-related macular degeneration (AMD)) from the fovea-centered cross sections in three-dimensional (3D) spectral domain optical coherence tomography (SD-OCT) images. In aspects, the subject innovation can determine the probability that that one or more types of pathology (e.g., ME, MH, AMD, etc.) are present in a given macular cross-section. Embodiments of the innovation can improve the efficiency of OCT-based analysis in daily clinical practice, both for online diagnostic reference and for offline slice tagging and retrieval.

Turning to the figures, FIG. 1 illustrates an example system 100 capable of determining the presence or absence of one or more retinal pathologies. Although the example system 100 shown in FIG. 1 contains all of the components discussed in connection with FIG. 1, it is to be appreciated that in various embodiments of the subject innovation, some or all of these components need not be included. System 100 can include an optical coherence tomography (OCT) system 102 capable of obtaining or capturing OCT images. In various embodiments, systems and methods discussed herein can be incorporated into systems capable of obtaining OCT images, or can be "stand-alone" systems capable of performing the processing and analysis discussed herein based on images obtained separately.

Figure 2:
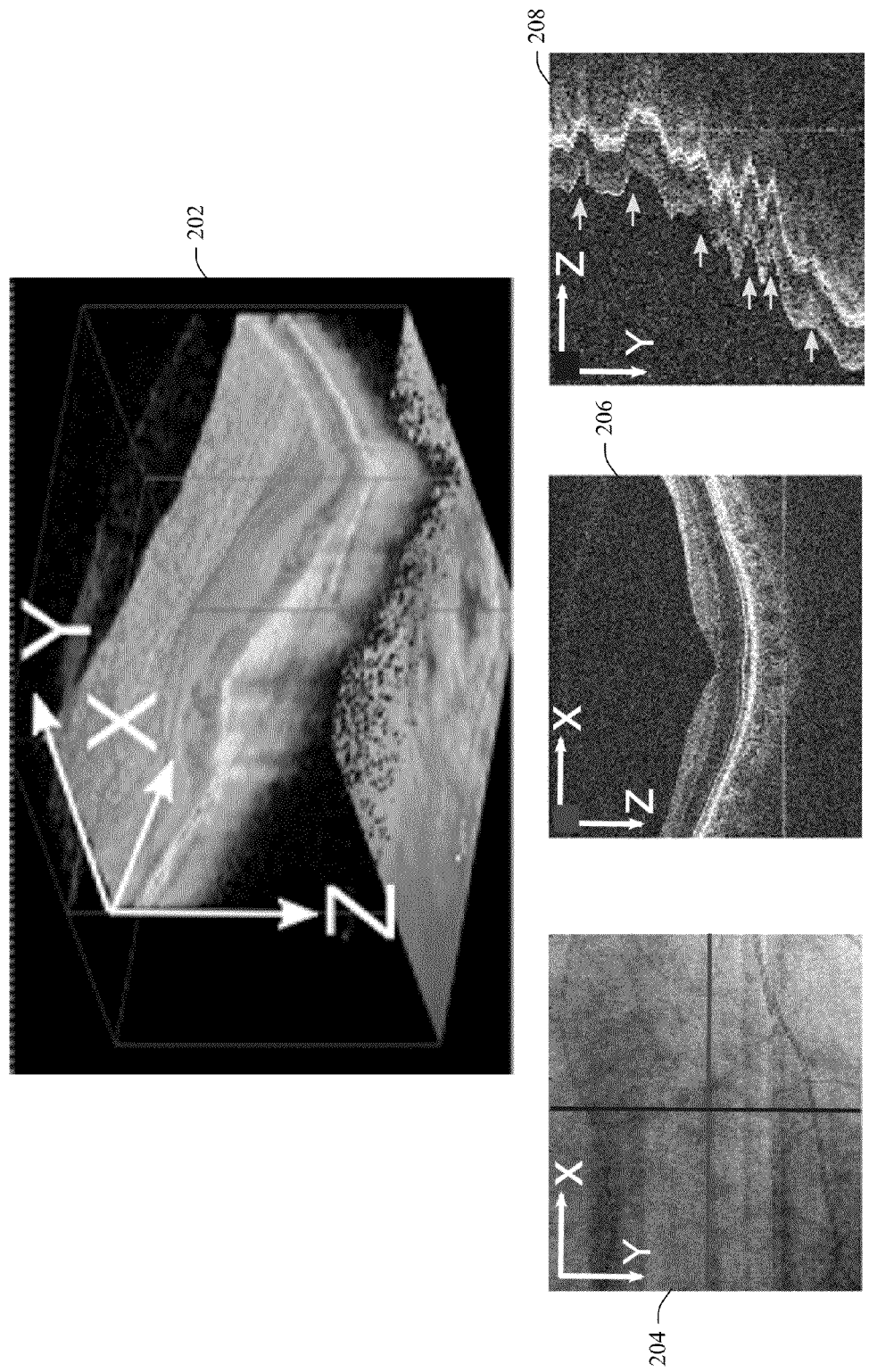
FIG. 2 shows an example 3-dimensional (3D) OCT macular scan image without eye motions and 2-dimensional projections.

For purposes of illustration and reference, FIG. 2 shows an example 3-dimensional (3D) OCT macular scan image 202 without eye motions, with horizontal (x), vertical (y), and depth (z) directions indicated on the image. Image 204 is an example 2-dimensional (2D) OCT en-face image (or OCT fundus image) generated by projecting a 3D macular OCT image along the z-axis, in the x-y plane. Image 206 shows a horizontal cross-sectional image in the x-z plane, corresponding to the red-line on the en-face image 204. Image 208 shows a vertical cross-sectional image corresponding to the blue-line on the en-face image. Significant z-directional eye motions (indicated by the yellow arrows), which can corrupt the spatial integrity of the 3D data, can be seen in image 208. In the ideal motion-free case, image 208 would look similar to a rotated version of image 206.

Returning to the discussion of FIG. 1, in various aspects, system 100 can also include a selection component 104 that can select one or more 2D images (or "slices") of a 3D OCT image for alignment, analysis, etc., such as those of image 206 in FIG. 2. These one or more slices can be selected in a variety of ways. For example, analytical techniques discussed herein can be used to determine one or more slices that have a high likelihood of passing through a region of interest (e.g., centered at the fovea, etc.), based on a library or database of OCT images and corresponding slices. In another example, each slice of the 3-D OCT image can be selected (e.g., sequentially, etc.), to be aligned, analyzed, etc. in reference to a database of similar slices. In other embodiments of system 100, selection component 104 need not be included, and the selection of individual slices can be performed otherwise, for example, by a user.

Additionally, system 100 can include an alignment component 106 that can apply one or more alignment techniques to a slice or image selected (such as by selection component 104, etc.) in order to obtain an aligned image to facilitate further analysis, classification, etc. These one or more alignment techniques can include any of those discussed herein, including applying a threshold to the original image, applying a filter (e.g., a median filter, etc.), using morphological closing and/or opening, curve fitting, warping or mapping the image based at least in part on the fitted curve, etc. If more than one image or slice is selected, each can be aligned using the techniques discussed herein.

Feature construction component 108 can be included in system 100, and can facilitate construction of features of an image or slice (such as those aligned by alignment component 106, etc.), by determining at least one global representation and/or at least one local descriptor based on the slice or image. Examples of global representations discussed herein include spatial divisions, including (multi-scale) spatial divisions, for example, those based on spatial pyramids (SP), such as a multi-scale spatial pyramid (MSSP). Local descriptors can include any of several types of local binary pattern (LBP), and dimensional reductions thereof, etc. Additionally, feature construction component 108 can apply an edge detector (e.g., Canny or other methods such as first order methods, higher order methods, phase congruency, etc.) to generate an edge map from the image or slice, and can determine global representations and/or local descriptors for the edge map.

Additionally, system 100 can include a classification component 110 that can include one or more classifiers (e.g., SVMs, etc.) that can be trained based on reference data. The one or more classifiers (e.g., SVMs, etc.) can be nonlinear, and can include 2-class classifiers (e.g., SVMs, etc.), such that each can classify between categories associated with an ocular pathology (e.g., ME, MH, AMD, etc.), such as the presence or absence of a pathology, or between different classifications or sub-categories within a pathology (e.g., early or advanced, full hole MH or pseudo-hole MH, etc.), etc. Alternatively, an n-class classifiers (e.g., SVMs, etc.) wherein n is greater than 2 can be employed, for example, to classify between the absence of a pathology and two or more different classifications within a pathology (e.g., no MH, pseudo-hole MH, or full hole MH; or "absent", "early" or "advanced"; etc.).

In some embodiments, system 100 can also include a database 112 that can comprise reference data for training one or more classifiers (e.g., SVMs, etc.), such as those of classification component 110. Database 112 can be local or remote, and can facilitate training (e.g., initially, periodically, intermittently, etc.) of the one or more classifiers (e.g., SVMs, etc.). In aspects, database 112 can be updated to include additional training data, based on which the one or more classifiers (e.g., SVMs, etc.) can be retrained, to increase accuracy of the one or more classifiers (e.g., SVMs, etc.). In other aspects, system 100 need not include database 112, and the classifiers (e.g., SVMs, etc.) (e.g., those of classification component 110) can be trained initially.

System 100 can also include an output component 114 that can present results to a user. These results can include one or more determinations as to whether each of a plurality of pathologies (e.g., ME, MH, AMD, etc.) is likely present, one or more probabilities associated with the one or more pathologies, one or more likely classifications (or associated probabilities) associated with the one or more pathologies, etc. Additionally, images used to obtain the one or more likelihoods or probabilities can be provided as well, and can be presented in original or, additionally or alternatively, modified or derived versions discussed herein (e.g., aligned, edge map, etc.).

As discussed herein, the approach to automated pathology identification can be based on the analysis of 2D slices from the macular OCT volume, such as image 206 of FIG. 2. This analysis can include, inter alia, analysis methods and techniques discussed herein, actions done by alignment component 106, feature construction component 108, classification component 110, etc. Slice-based analysis can be 2D slice-based analysis is consistent with existing clinical practice in ophthalmology. Clinicians routinely examine the OCT volume in a slice-by-slice manner, for example by using the en-face view illustrated in image 204 as a guide for selecting and viewing slices. Thus, the ability to analyze and display information about pathologies in a slice-based manner is aligned with existing practices. Additionally, the 3D OCT data itself is naturally organized as a series of slices corresponding to a sequence of x-z scans. Within each slice, the OCT data is very consistent, as shown in image 206. However, a modern scanner can require around 2 s to image a target cube. During this period, misalignment across slices can occur due to the natural and involuntary movement of the subject's eyes. Involuntary movements include micro-saccade, ocular tremor and drifting, resulting in oscillations of up to 15 Hz. These motion artifacts can be seen in image 208 for a 2D slice that cuts across multiple horizontal scans. These inter-slice distortions and misalignments raise considerations relevant to a full 3D analysis of the OCT volume that are absent when analyzing individual slices such as image 206.

Figure 3:
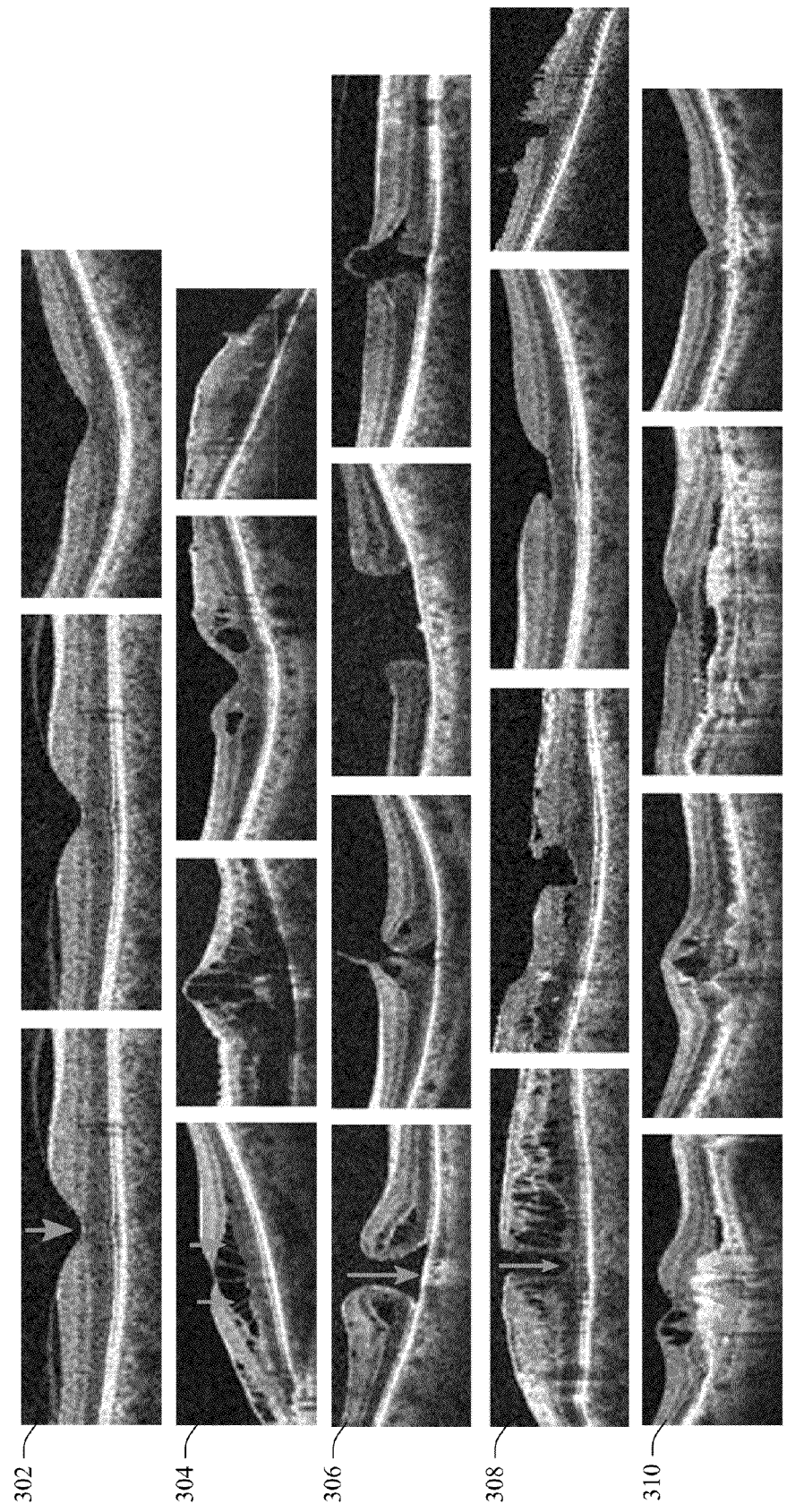
FIG. 3 shows example images illustrating the appearance for a normal macula, macular edema (MH), macular hole (MH), and age-related macular degeneration (AMD).
Figure 4:
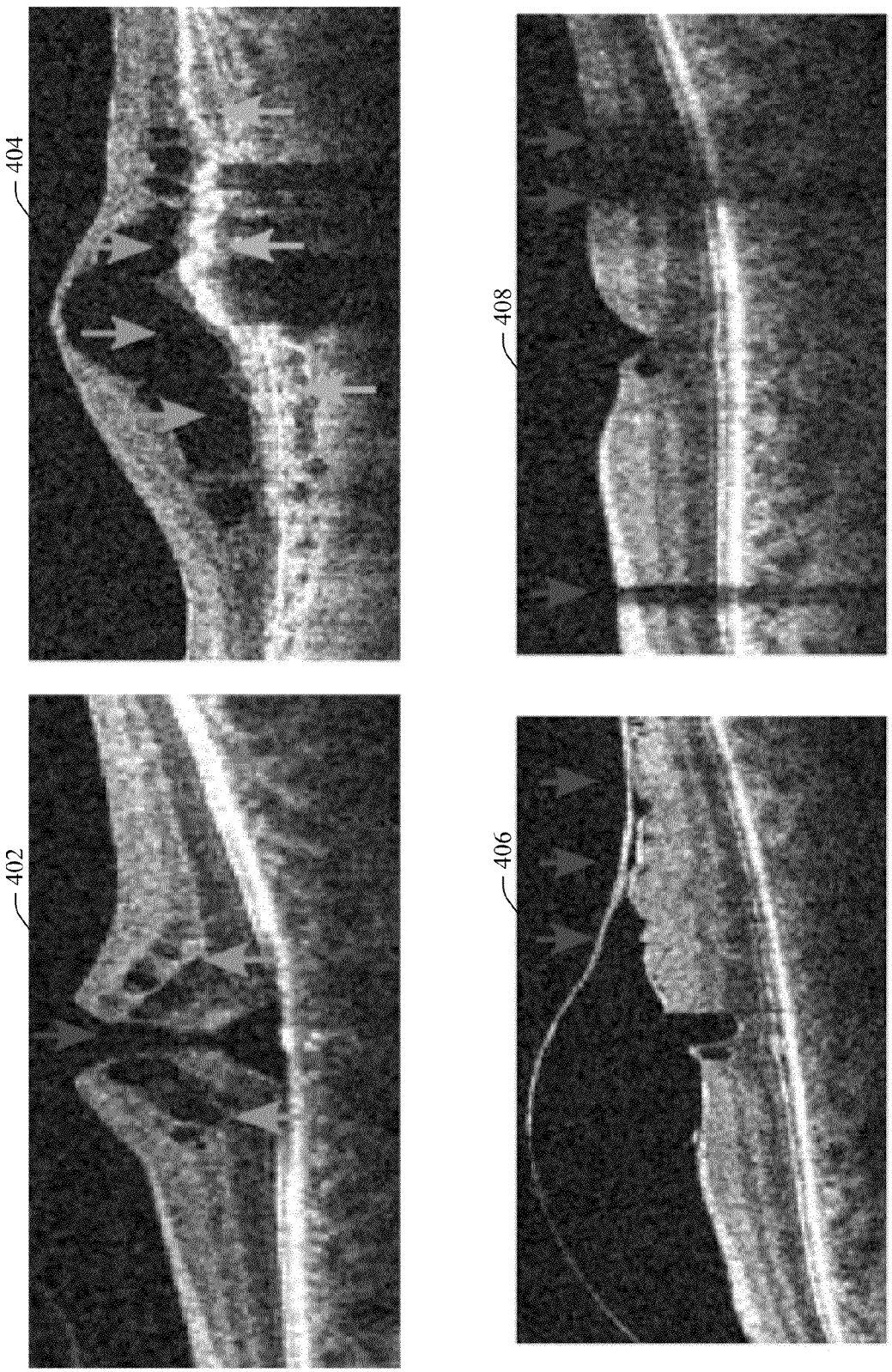
FIG. 4 shows images of multiple pathologies, with MH indicated by red arrows, ME by green, and AMD by blue.

The subject innovation comprises techniques that can automatically identify macular pathologies in a given x-z slice at a known anatomical position. These techniques can be used for identifying the presence of the normal macula (NM) and each of the following macular pathologies: macular edema (ME), macular hole (MH) (including full-thickness holes and pseudo-holes), and age-related macular degeneration (AMD), based on one or more x-z slices (e.g., one centered at the fovea (macula center), etc.). FIG. 3 shows example images illustrating the appearance for a normal macula and each pathology. Row 302 shows images of a NM, with a smooth depression shown at the center, as indicated by the arrow. Row 304 shows ME, with retinal thickening and liquid accumulation that appears as black blobs around the fovea in an OCT scan. Full-thickness MH is shown in row 306, and pseudo-hole MH in row 308. For pseudo-hole, the hole formation at the fovea does not reach the outermost retinal later (the retinal pigment epitherium (RPE)). Row 310 shows AMD; the irregular contours usually extrude in dome shapes, and appear at the bottom layer of the retina, the RPE. It should be noted that multiple pathologies can coexist in one eye. FIG. 4 shows images of multiple pathologies 402, 404, 406 and 408, with MH indicated by red arrows, ME by green, and AMD by blue. Additionally, detached tissue can be seen in image 406, and shadowing effects in image 408. In the case of multiple pathologies, the techniques of the subject innovation can report the existence of both pathologies.

In aspects, the subject innovation can also be used to differentiate subcategories within a pathology. For instance, referring again to FIG. 3, the MH category discussed herein contains both full-thickness holes (FH) (row 306) and pseudoholes (PH) (row 308). This distinction is clinically relevant, as these two cases are treated differently. The subject innovation can be used to discriminate between subcategories, for example, these two subtypes within the MH category, as shown by results discussed further herein.

Automated pathology identification in ocular OCT images can be complicated by four factors. First, the co-existence of multiple pathologies or other pathological changes (e.g., epiretinal membrane, vitreous hemorrhage, etc.) can complicate the overall appearance, making it challenging to model each pathology individually. Second, there can be high appearance variability within each pathology, e.g., in MH cases, the holes can have different widths, depths, and shapes, and some can be covered by incompletely detached tissues, making explicit pathology modeling difficult. Third, the measurement of reflectivity of the tissue is affected by the optical properties of the overlying tissues, e.g., opaque media in the vitreous area or blood vessels around retinal surfaces will block or absorb much of the transmitted light respectively, and thus produce shadowing effects. Fourth, a portion of the image may have lower quality due to imperfect imaging. As a result of these factors, attempts to hand-craft a set of features or rules to identify each pathology are unlikely to generalize well. Instead, the subject innovation can include direct encoding of the statistical distribution of low-level image features and training discriminative classifiers based on a large expert labeled dataset as discussed further herein, and can thus achieve more robust performance.

Aspects of the subject innovation provide systems and methods that can make diagnostic suggestions solely based on the interpretation of image appearances, so as to provide for OCT image interpretation. The subject innovation can aid clinical diagnosis, by providing image analysis information that can combined with other available information (e.g., the results of OCT image analysis in conjunction with other ancillary tests), which, when considered together, can be used to make a final diagnostic decision.

While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

Figure 5:
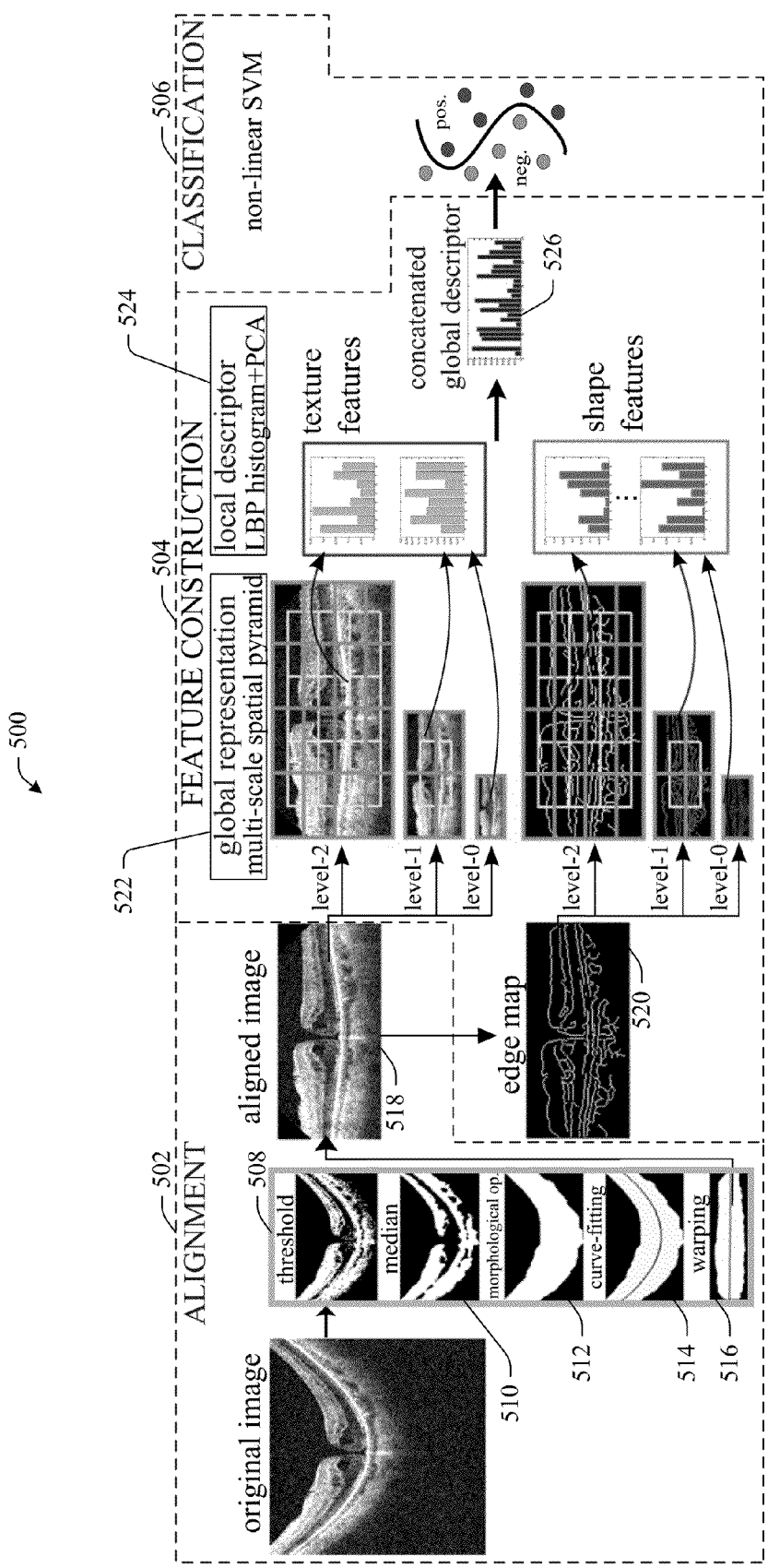
FIG. 5, there is illustrated a methodology of OCT image analysis in accordance with an embodiment of the innovation.

Referring now to FIG. 5, there is illustrated a methodology 500 of OCT image analysis in accordance with the innovation. The method 500 of FIG. 5 can be combined with other steps or acts described herein, such as capturing of one or more OCT images, selection of one or more OCT images for analysis, outputting of results, etc. Method 500 can consist of three steps (each of which can contain sub-steps), which are illustrated in FIG. 5, with each enclosed within dashed boundaries. First, image alignment can be performed at 502 on a selected OCT image, to reduce the appearance variation across scans. Second, feature construction can be performed on the aligned image at 504, wherein a global descriptor for the aligned image and its corresponding edge map can be determined, such as by computing spatially-distributed multi-scale texture and shape features. A spatial pyramid (SP), for example, a multi-scale spatial pyramid (MSSP) (or other spatial division or (multi-scale) spatial division), can be used to encode the global spatial organization of the retina. To encode each spatial block in the spatial division or (multi-scale) spatial division (e.g., SP or MSSP, etc.), a dimension-reduced local binary pattern (LBP) histogram can be employed to capture the texture and shape characteristics of the retinal image. This feature descriptor can preserve the geometry as well as textures and shapes of the retinal image at multiple scales and spatial granularities. At step 506, a non-linear classifier (e.g, SVM, etc.) can be employed for each of one or more classifications (e.g., presence or absence of each pathology, multiple subtypes within a given pathology, etc.). In one embodiment, the classifiers (e.g., SVMs, etc.) can be 2-class classifiers (e.g., SVMs, etc.), while in other embodiments, n-class (with n greater than 2) classifiers (e.g., SVMs, etc.) can be employed. During a training run, step 506 can comprise training the one or more classifiers (e.g., SVMs, etc.) based on reference images, while in a testing run, step 506 can comprise classifying an unknown image into a class for each of at least a subset of the classifiers (e.g., SVMs, etc.). In general, step 506 can comprise separate acts of training and testing or classifying.

Step 502, alignment of the OCT image of the retina, can include multiple acts. Imaged retinas can have large variations in their inclination angles, positions, and natural curvatures across scans, as shown in the retinal slice images of FIGS. 2-5. It can therefore be helpful to roughly align the retinas to reduce these variations before constructing the feature representation in step 504. To this end, a heuristic procedure can be used to flatten the curvature and center the retina. At step 508, the method can threshold the original image to detect most or a majority of the retina structures; at 510, the method can include the act of applying a median filter to remove noise and thin detached tissues; at 512, the method can include the act of finding the entire retina by using morphological closing and then opening (by closing, black blobs (e.g., cystoid edema, etc.) inside the retina can be filled, and by opening, thin or small objects outside the retina can be removed); at 514, the found retina area can be fit with a curve (e.g., a second-order polynomial, etc.) using least-square curve fitting (a low order polynomial (e.g., degree 2) can avoid overfitting, and thus preserve important shape changes caused by pathologies); and at step 516, the method can include the acts of warping the entire retina to be approximately horizontal by translating each image column a distance according to the fitted curve of step 514 (after the warping, the fitted curve will become a horizontal line) and cropping the warped retina in the z-direction with a reserved margin (as seen in the aligned image 518).

Figure 6A:
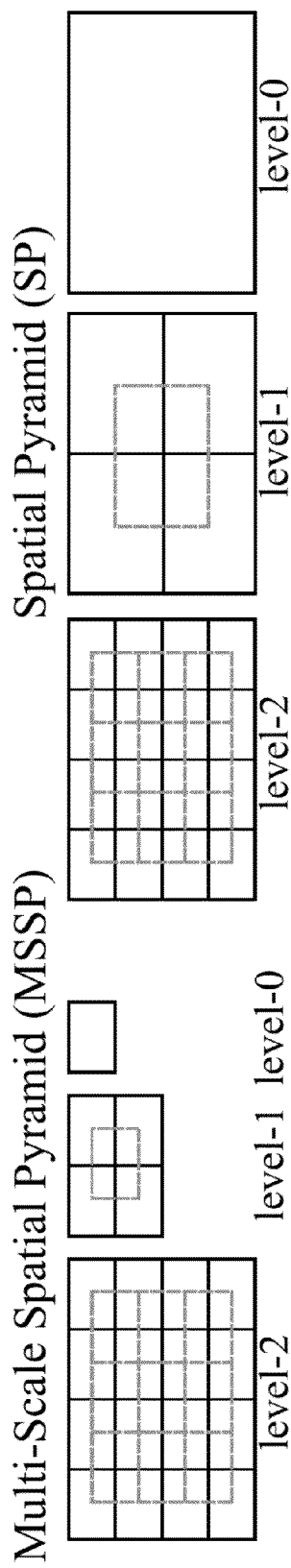
FIG. 6A illustrates the differences between a 3-level multi-scale spatial pyramid (MSSP) and a 3-level spatial pyramid (SP).

Step 504, feature construction, can comprise multiple steps. An edge map (Canny, etc.) can be constructed, such as edge map 520. At 522, a global representation can be constructed based on the aligned image 518 and corresponding edge map 520. This global representation can be a spatial division or (multi-scale) spatial division, such as a spatial pyramid (SP) or a multi-scale spatial pyramid (MSSP). The choice of a global spatially-distributed feature representation for OCT imagery based on MSSP can provide advantages. First, pathologies are often localized to specific retinal areas, making it important to encode spatial location. Second, the context provided by the overall appearance of the retina is important for correct interpretation; e.g., in image 408, it can be easier to distinguish between a shadow and a macular hole more effectively given the context of the entire slice. Third, pathologies can exhibit discriminating characteristics at both small and large scales; therefore, representing both micro-patterns and macro-patterns provides information from each. For these reasons, a global multi-scale image representation which preserves spatial organization can be used. The MSSP can capture the geometry of the aligned retina at multiple scales and spatial resolutions. FIG. 6A illustrates the differences between a 3-level MSSP and a 3-level SP. To form a k-level MSSP, for each level l ($0 \leq l \leq (k-1)$), the original image can be rescaled by $2^{l-k+1}$ using bilinear interpolation, and the rescaled image can be divided into $2^l$ blocks in both image dimensions. The local features computed from all spatial blocks can be concatenated in a predefined order to form an overall global descriptor, as illustrated in FIG. 5 at 526. Optionally, the features from the overlapped blocks (the green blocks in FIG. 6A) can be added to reduce boundary effects.

Figure 6C:
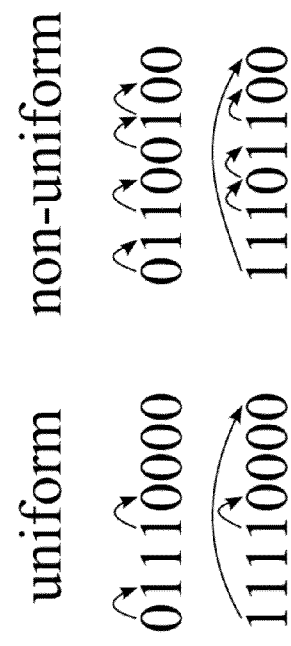
FIG. 6C illustrates two examples each of uniform patterns and non-uniform patterns.
Figure 6B:
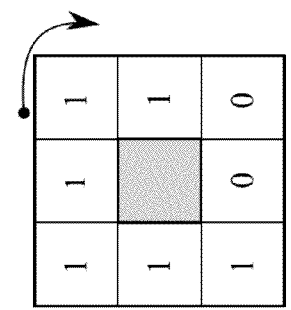
FIG. 6B illustrates the computation of a local binary pattern (LBP).

Turning to step 524, a local descriptor can be determined, such as local binary pattern (LBP). LBP is a non-parametric kernel that can summarize the local structure around a pixel. Any of several types of LBP can be used, including $LBP_{8,1}$, which can capture the micro-patterns that reside in each local block. The $LBP_{8,1}$ operator derives an 8 bit binary code by comparing the center pixel to each of its 8 nearest neighbors in a 3×3 neighborhood, while "1" represents radius 1 when sampling the neighbors. The resulting 8 bits are concatenated circularly to form an LBP code in the range [0255]. FIG. 6B illustrates the computation of $LBP_{8,1}$ at item 602. Formally, equation (1) represents $LBP_{8,1}$:

$$LBP_{8,1} = \sum_{n=0}^{7} f(v_n - v_c) 2^n \qquad (1)$$

where $f(x)=1$ if $x \geq 0$, otherwise $f(x)=0$; $v_c$ and $v_n$ represent the pixel value at the center and the neighboring pixel, respectively, with each neighbor being indexed circularly.

For each block of pixels in the MSSP, the histogram of LBP codes can be computed to encode the statistical distribution of different micro-patterns, such as spots, edges, corners, and flat areas. Histogram descriptors can be effective at aggregating local intensity patterns into global discriminative features. In particular, they avoid the need to precisely localize discriminating image structures, which can be difficult in complex and highly variable OCT images. Since the LBP histogram can be computed in multi-scale image blocks, the distribution of both micro-patterns and macro-patterns can be encoded, in contrast to conventional systems and methods.

Although a single $LBP_{8,1}$ histogram has only 256 bins, the concatenation of histograms from each block to form the global feature vector can result in an impractically high dimension. The dimension of the LBP histogram can be reduced in a variety of ways, such as by applying principal component analysis (PCA), yielding a dimensionally reduced descriptor referred to as $LBP_{8,1}^{pca}$ herein.

Figure 7:
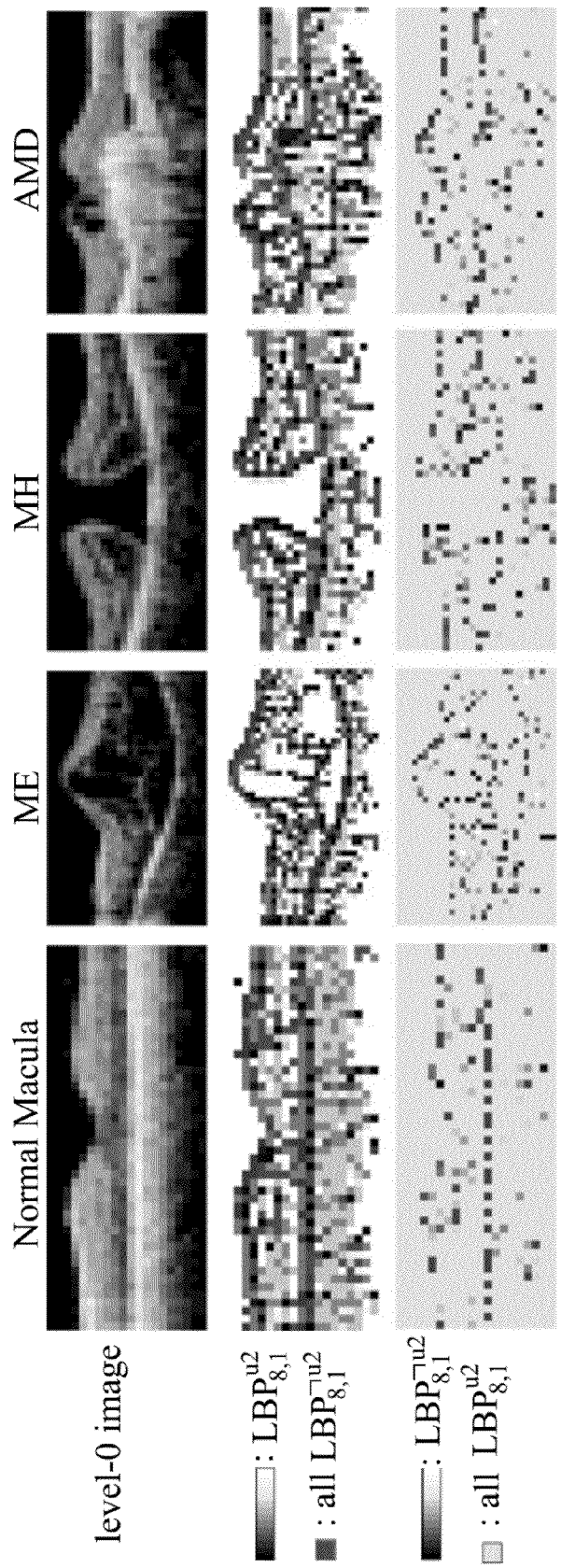
FIG. 7 shows images indicating visualizations of uniform and non-uniform LBPs on example level-0 images.

In other embodiments, alternative approaches to dimensionality reduction, for example, uniform LBP (referred to herein by $LBP_{8,1}^{u2}$), can be used. An LBP pattern is called "uniform" if it contains at most two bitwise transitions, as shown in FIG. 6C, which illustrates two examples each of uniform patterns and non-uniform patterns. A histogram of $LBP_{8,1}^{u2}$ can be formed by retaining occurrences of each of 58 uniform patterns and putting all occurrences of 198 non-uniform patterns (denoted by $LBP_{8,1}^{-u2}$) to a single bin, resulting in 59 bins in total. $LBP_{8,1}^{u2}$ has been shown to occupy 90% of all $LBP_{8,1}$ patterns in pixel count, when computed from image textures. However, when LBP codes are computed in the rescaled images, $LBP_{8,1}^{u2}$ may no longer be in the majority. Also, the distribution of individual $LBP_{8,1}^{u2}$ patterns can contain important distinctive information for category discrimination, in spite of its low frequency of occurrences. For reference, FIG. 7 shows images indicating visualizations of $LBP_{8,1}^{u2}$ and $LBP_{8,1}^{-u2}$ on example level-0 images. All $LBP_{8,1}^{-u2}$ are shown in red in the 2nd row of FIG. 7, and the individual $LBP_{8,1}^{-u2}$ codes are shown in gray-level in the 3rd row. Although $LBP_{8,1}^{-u2}$ patterns have low counts, most of them reside in the important contours and can therefore be useful for discrimination. Experimental results discussed herein found superior performance of $LBP_{8,1}^{pca}$ when compared to other LBP-based features (e.g., $LBP_{8,1}^{u2}$, $LBP_{8,1}^{-u2}$, etc.).

Figure 8:
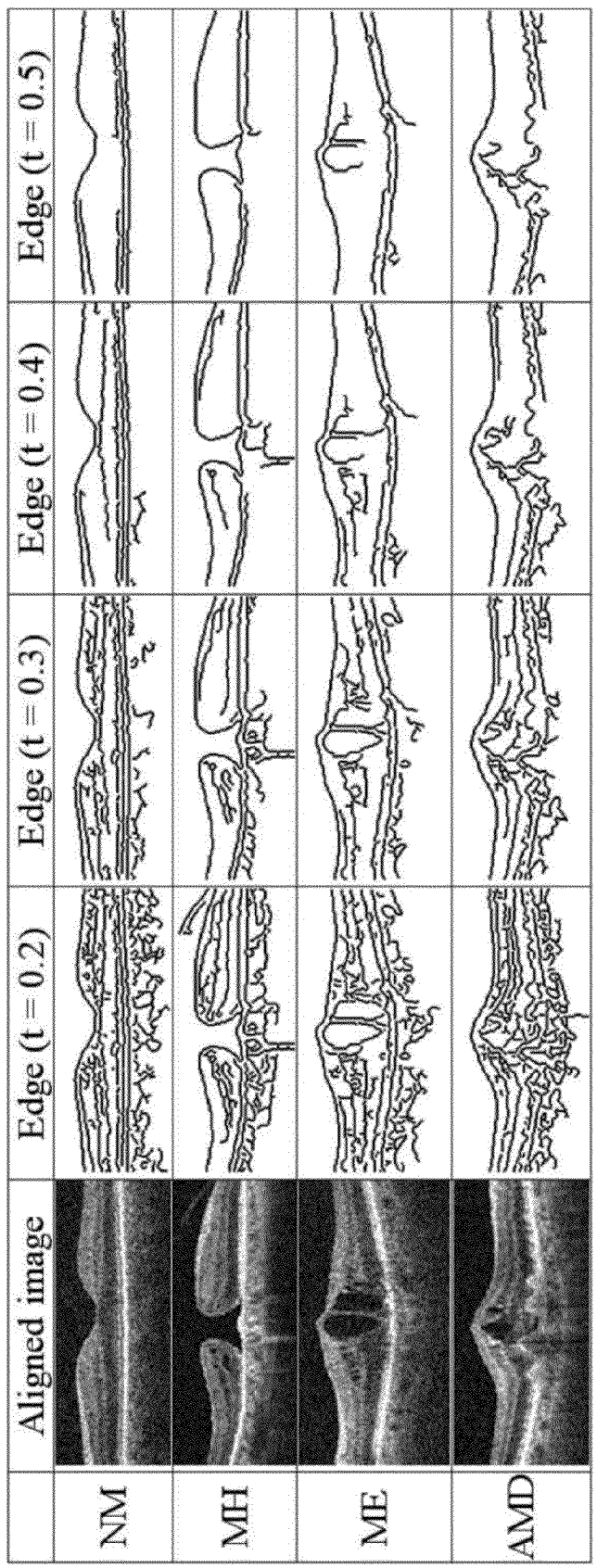
FIG. 8 shows example edge maps for each of NM, ME, MH, and AMD for a variety of edge detection thresholds.

As discussed above, LBP-based features (e.g., $LBP_{8,1}^{pca}$, etc.) can be applied to images to encode the texture property of the aligned image. In addition, capturing the shape characteristics of the retinal image in conjunction with the textures can be useful so that different properties are represented in the descriptor. To encode the shape characteristics (i.e., the encoding of edge and contour information), an edge map (e.g., Canny, etc.) 520 can be generated from the aligned retinal image, and then LBP-based features (e.g., $LBP_{8,1}^{pca}$, etc.) can be computed for each spatial block in the spatial division or (multi-scale) spatial division (e.g., SP or MSSP, etc.) representation of the edge map 520, as illustrated in FIG. 5. FIG. 8 shows example (Canny) edge maps for each of NM, ME, MH, and AMD for a variety of edge detection thresholds. Since edge maps generated from varied edge detection thresholds (where smaller edge detection thresholds t retain more images) are different in edge quantity, experiments discussed herein test a variety of edge detection thresholds to determine optimal settings. From the edge maps in FIG. 8, it can be observed that when $t \geq 0.3$ most spurious details are suppressed, while the high-contrast boundaries become prominent. In fact, a skilled observer can identify some pathologies just from the edge map. In MH, for example, a hole contour can clearly be seen around threshold $t=0.4$. Thus, it is possible that utilizing the shape features alone is sufficient for some categories, and results discussed further herein examine the effect of using texture or shape features alone, or in combination, in order to identify which feature type is more discriminative for a specific pathology.

LBP histograms can be a powerful tool in preserving the contents of a binary image, such as an edge map or a silhouette image. LBP-based features provide a reconstruction ability that cannot be easily achieved if the input histogram is the intensity or orientation histogram, since more pixel arrangements can map to the same histograms. Prior experimental results provide strong evidence that LBP histograms can preserve the structures in a binary image.

Finally, in step 506, at least one classifier (e.g., SVM, etc.) can be employed (e.g., a SVM with a radial basis function (RBF) kernel (e.g., Gaussian, etc.) and probabilistic output, etc.) for each pathology. In some embodiments, the at least one classifier (e.g., SVM, etc.) can be trained (for example, using a 1 vs. the rest approach) at step 506 (e.g., in a method to train one or more classifiers (e.g., SVMs, etc.)), whereas in other embodiments, the at least one classifier (e.g., SVM, etc.) can be used to classify one or more aligned images. The kernel parameter and error penalty weight of classifiers (e.g., SVMs, etc.) can be chosen based on a training or reference data set, for example, stored in database 112. In experiments conducted herein, the kernel parameter and error penalty weight of classifiers (e.g., SVMs, etc.) were chosen by cross validation on the training set. The probability scores from each pathology classifier can be compared to a set of decision thresholds to determine the corresponding sensitivity and specificity.

What follows is a more detailed discussion of certain systems, methods, and apparatuses associated with aspects of the subject innovation. To aid in the understanding of aspects of the subject innovation, theoretical analysis and experimental results associated with specific experiments that were conducted are discussed herein. However, although for the purposes of obtaining the results discussed herein, specific choices were made as to the selection of various aspects of the experiments and associated setups or techniques—such as the choice of specific analytical techniques, as well as other aspects—the systems and methods described herein can be employed in other contexts as well. For example, aspects of the subject innovation can utilize other global representations or local descriptors, although the experiments discussed below only utilize MSSP and $LBP_{8,1}$ (and dimensionally reduced $LBP_{8,1}$). As examples, a different spatial division or (multi-scale) spatial division can be used, such as a different level MSSP (e.g., greater than 3-level), or overlap blocks can be included or excluded, etc. In another example, different selections of OCT images may be chosen, or classifiers (e.g., SVMs, etc.) could vary (e.g., in terms of kernel, etc.) from those used in the experiments discussed herein, which may lead to differing results, as explained in greater detail below.

In experiments conducted herein, a sample of SD-OCT macular scans were obtained from healthy subjects and subjects with MH and/or ME and/or AMD in a first dataset (Dataset A) used for development, training, and some testing (this dataset included 326 scans from 136 subjects (193 eyes)); and in a second dataset (Dataset B) for further testing (involving 131 scans from 37 subjects (58 eyes)). The study subjects were enrolled at the University of Pittsburgh Medical Center Eye Center or at the New England Eye Center. All subjects had comprehensive ophthalmic examination followed by SD-OCT macular cube scan. A fovea-centered cross-sectional slice for each of SD-OCT images was encoded using spatially-distributed multi-scale texture and shape features. Three ophthalmologists labeled each fovea-centered slice independently and multiple grounds truth were determined and compared based on the labeling (e.g., a single opinion, majority opinion, unanimous opinion, etc.). Machine learning algorithms were used to identify the discriminative features automatically. Classifiers (2-class SVMs in the experiments, although non-SVM classifiers or multi-class classifiers (e.g., SVMs, etc.) can be employed) were trained to identify the presence of normal macula and each of MH, ME, and AMD separately. The area under the receiver operating characteristic curve (AUC) was calculated to assess the performance.

The studies were approved by the Institutional Review Board committees of the University of Pittsburgh, Pittsburgh, Pa. and Tufts Medical Center, Boston, Mass., and adhered to the Declaration of Helsinki and Health Insurance Portability and Accountability Act regulations, with informed consent obtained from all subjects.

In one study, Dataset A, consisting of 326 macular spectral-domain OCT scans from 136 subjects (193 eyes), was used for training and testing. The original resolution of the scans was either 200×200×1024 or 512×128×1024 in 6×6×2 mm volume (width (x), height (y) and depth (z)). All horizontal cross-section images (x-z slice) were rescaled to 200×200 to smooth out noise while retaining sufficient details for pathology identification. For each of the 326 scans, the x-z slice crossing through the foveal center was then selected by an expert ophthalmologist.

Figure 9:
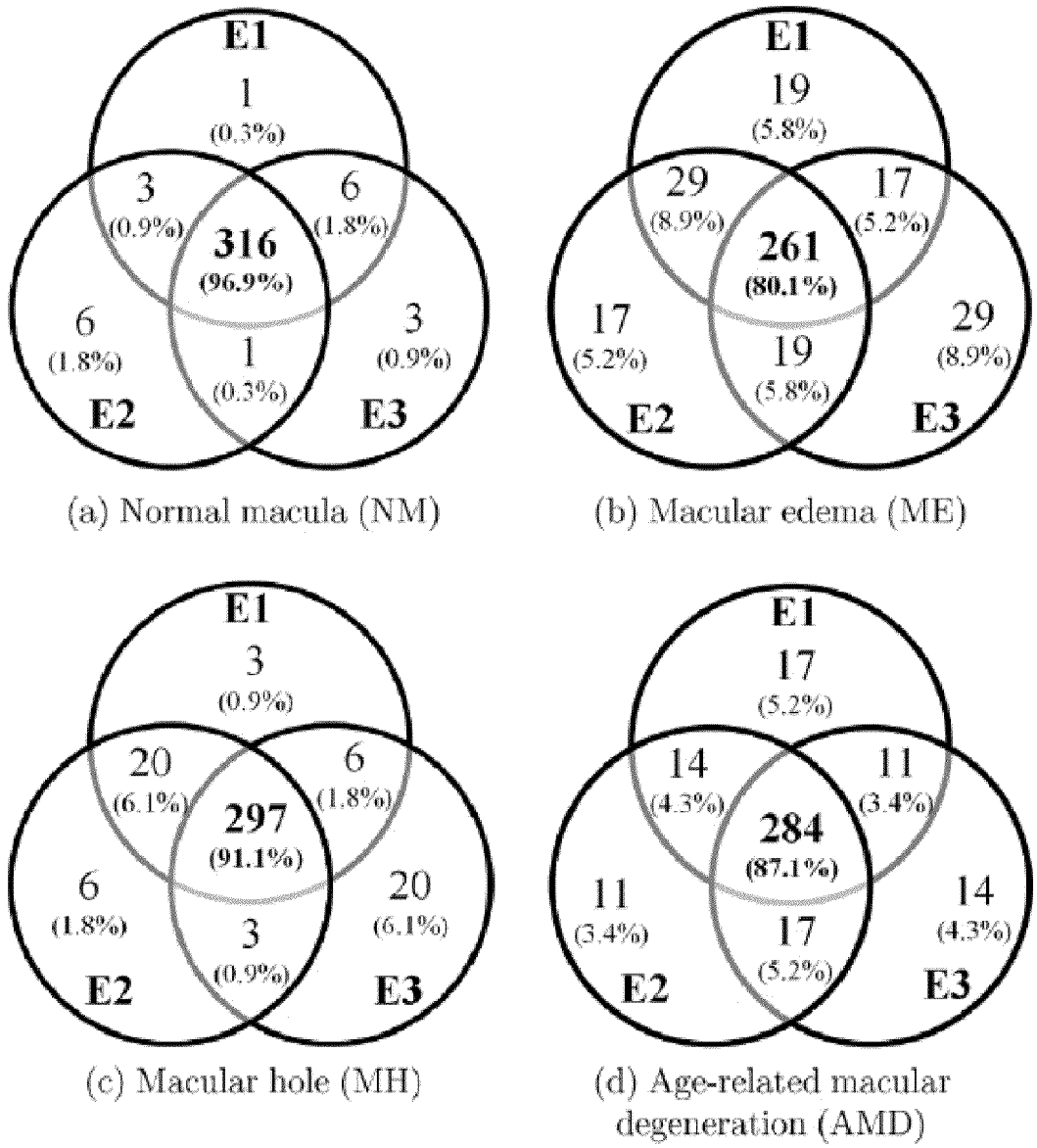
FIG. 9 illustrates the labeling agreement among three experts via Venn diagrams for each of NM, ME, MH, and AMD.

Three OCT experts then independently identified the presence or absence of normal macula and each of ME, MH, and AMD in the fovea-centered slice. Note that multiple pathologies can coexist in one slice. FIG. 9 illustrates the labeling agreement among the three experts via Venn diagrams for each of NM, ME, MH, and AMD. The complete agreement among the experts for NM, ME, MH, and AMD was 96.9%, 80.1%, 91.1%, and 87.1%, respectively, where a lower agreement was observed for ME and AMD. The majority opinion of the three experts' labeling was computed separately for each pathology and used as the ground truth. Table 1 shows the number of positive images for each pathology category as defined by the ground truth:

TABLE 1

(Number of positive scans, eyes, and subjects, as defined by majority opinion)

| Statistics | NM | MH | ME | AMD |
|---|---|---|---|---|
| Scan | 81 | 74 | 203 | 74 |
| Eye | 66 | 36 | 116 | 37 |
| Subject | 65 | 33 | 90 | 26 |

In Table 1, for a specific pathology, an eye or subject that had at least one positive scan was counted as positive.

The Kappa statistics (k) were calculated to assess the pair-wise experts' labeling agreement, as listed in Table 2:

TABLE 2

(Kappa statistics of pair-wise expert labeling for experts E1, E2, and E3)

| Kappa (k) | NM | MH | ME | AMD |
|---|---|---|---|---|
| E1, E2 | 0.94 | 0.92 | 0.76 | 0.76 |
| E1, E3 | 0.97 | 0.78 | 0.69 | 0.73 |
| E2, E3 | 0.93 | 0.76 | 0.71 | 0.77 |

As seen in Table 2, all kappa values for identification of normal macula were high (all k>0.93) and for MH, the kappa value from one expert-pair (expert 1 and 2) was high (0.92). However, all kappa values for ME and AMD were within 0.61-0.80 range, which represented substantial but imperfect agreement.

Table 3 lists the scan statistics for each combination of the three pathologies:

TABLE 3

(Number of positive scans, eyes, and subjects per majority opinion for each combination)

| Statistics | Single Pathology Only | | | Combination of Pathologies | |
|---|---|---|---|---|---|
| | ME | MH | AMD | ME + MH | ME + AMD |
| Scan | 93 | 9 | 29 | 65 | 45 |
| Eye | 65 | 3 | 15 | 34 | 25 |
| Subject | 53 | 3 | 13 | 32 | 19 |

As seen in Table 3, no subjects in Dataset A had all three pathologies, although it is possible. Additionally, Table 3 shows that ME often co-occurs with MH or AMD.

Figure 10:
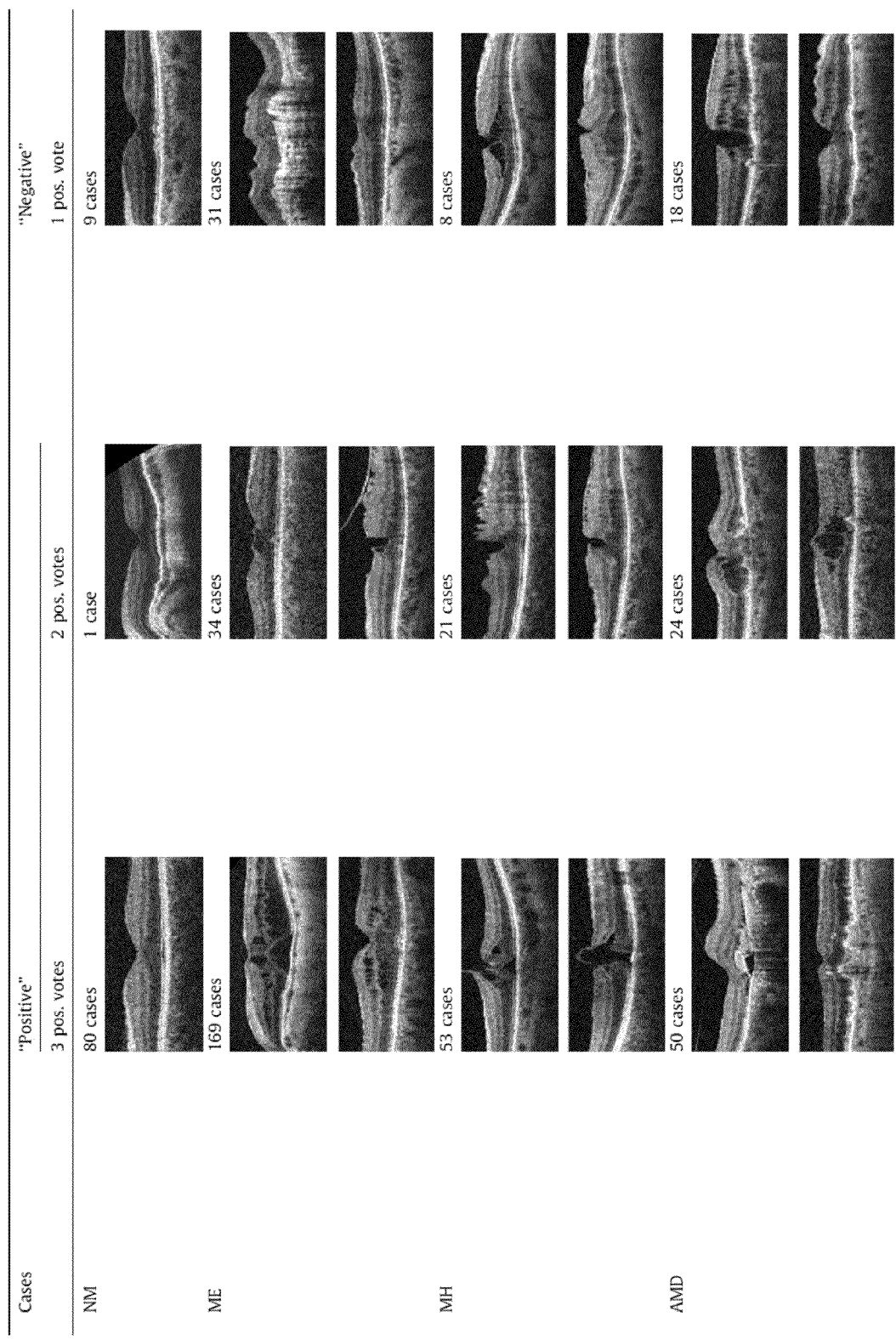
FIG. 10 illustrates statistics and several representative examples of consistently and inconsistently labeled images for each pathology.

FIG. 10 illustrates statistics and several representative examples are shown for each pathology, where all three experts, only two experts, or just one expert gives a "positive" label, in order to further show how many positive/negative cases result from inconsistent labeling. The images labeled as positive by only one expert were treated as negative instances given the use of majority opinion for ground truth (although, with a different ground truth, e.g., 1 or more experts, these images would count as positive). The quantity of images having one positive vote was considerably larger for ME and AMD (31 and 18 cases, respectively), revealing greater ambiguity in their identification. Images without complete agreement frequently contained early pathologies occupying small areas.

The study proceeded according to the analytical steps discussed in connection with FIG. 5: alignment, feature construction, and classification (training, testing, or a combination of the two). The alignment preprocessing step used an intensity threshold 60, 5×5 median filter, disk-shaped structure element with size 30 for morphological closing and size 5 for opening, and 15 pixel reserved margin at both top and bottom when cropping the retinal area in the z-direction. These settings were found to be able to roughly remove the curvature and center the retina area in all images in the dataset.

The study used 10-fold cross validation at the subject level, where for each fold, 10% of positive and negative subjects were put in the test set. All images from the same subject were put together in either the training or test set. Images from left eyes or right eyes were not separated, but trained and tested together. In order to further enrich the training set, both the training image and its horizontal flip were used as the training instances. The 10-fold testing results were aggregated and the area under the receiver operator characteristic curve (AUC) was computed (since the 10-fold data splitting was at the subject level, while each subject could have a different number of scans, each fold could have quite different scan counts. Thus, the 10-fold results were aggregated to compute one overall AUC). Although some subjects or eyes contributed more than one scan to the image library, these scans were taken on different dates and usually showed pathological progression or additional pathologies. Because of this, each scan was treated as a different instance, and the AUC result was reported at the scan level. To get a more reliable assessment of the performance, the 10-fold data splitting procedure was repeated six times, where each time a different data splitting was generated randomly, and the mean and standard deviation of the 6 AUCs were computed as the performance metric.

To test the statistical significance of the performance difference between different algorithmic settings, the DeLong test was adopted to compare their receiver operating characteristic (ROC) curves. The DeLong test is widely used in biomedical research, takes into account the correlation of the diagnostic results from different algorithms for the same test units, and can generate an estimated covariance matrix of algorithm performance, which can be used for statistical testing. The test was applied in the following way: if, under the DeLong test, one setting was found to be superior to than another at p=0.05 significant level for all 6 different data-splitting procedures, then the performance of the best setting was determined to be significant.

Next, local descriptors were analyzed. To validate the use of dimension-reduced LBP histograms as local features, the texture properties of the aligned retinal image were encoded, and the resulting performance was compared to several other popular descriptors, including mean and standard deviation of intensity (MS), intensity histogram (I), and orientation histogram (O). Each feature type was employed with a 3-level MSSP with overlapped blocks (if the feature dimension of the block descriptor is d, a 3-level MSSP with the overlapped blocks will result in a global descriptor of length d×31, where 31 is the total number of blocks), although other (multi-scale) spatial divisions (or non-multi-scale, e.g., SP) can be used. The orientation histogram was formed from the gradient direction and magnitude computed from 2×2 neighborhoods. For I and O features, the quantization of 32 bins in intensity and angle, respectively, was used, since this produced the best results. For LBP histograms, the intensity image was quantized to 32 levels before LBP encoding in order to suppress pixel noise; this quantization improved the accuracy of LBP by about 0.7% on average. For $LBP_{8,1}^{pca}$ computation, the principle axes were derived from the training images of each fold separately.

In feature computation, for NM, ME, and AMD, the highest level features (the 2nd-level in a 3-level MSSP) were computed from the aligned image directly; for MH, these features were encoded from the further rescaled image (half size in width and height) instead. This rescaling for MH resulted in better performance for all descriptors (1-5% improvement). This can be attributed to the macro-scale nature of holes, where details present in the original resolution are not required for identification.

The AUC results are listed in Table 4:

TABLE 4

(AUC results of different local block descriptors)

| AUC | MS (2) | I (32) | O (32) | $LBP_{8,1}^{u2}$ (59) | $LBP_{8,1}^{pca}$ (32) | $LBP_{8,1}^{pca}$ (59) | $LBP_{8,1}$ (256) |
|---|---|---|---|---|---|---|---|
| NM | 0.907 ± 0.004 | 0.916 ± 0.010 | 0.970 ± 0.003 | *0.972* ± 0.003 | 0.969 ± 0.002 | 0.970 ± 0.003 | 0.891 ± 0.003 |
| ME | 0.890 ± 0.006 | 0.906 ± 0.006 | 0.930 ± 0.005 | 0.933 ± 0.005 | 0.938 ± 0.003 | *0.939* ± 0.004 | 0.804 ± 0.033 |
| MH | 0.639 ± 0.010 | 0.692 ± 0.012 | 0.806 ± 0.011 | 0.836 ± 0.008 | 0.846 ± 0.011 | *0.856* ± 0.011 | 0.711 ± 0.013 |
| AMD | 0.830 ± 0.008 | 0.905 ± 0.006 | 0.919 ± 0.003 | *0.927* ± 0.005 | .0926 ± 0.009 | *0.927* ± 0.008 | 0.811 ± 0.011 |
| Ave. | 0.817 | 0.855 | 0.906 | 0.917 | 0.920 | *0.923* | 0.804 |

In Table 4, only the texture properties from the retinal image were encoded. The highest AUC values in each row are indicated in bold italics. The number in parentheses below each local block descriptor represents the feature dimension of the corresponding local descriptor.

The significance test results between $LBP_{8,1}^{pca}$ (59) and other descriptors are shown in Table 5:

TABLE 5

(Significance results between $LBP_{8,1}^{pca}$(59) and other descriptors under DeLong test)

| Sig. Test | $LBP_{8,1}^{pca}$(59) | | | | |
|---|---|---|---|---|---|
| | M, S | I | O | $LBP_{8,1}^{u2}$(59) | $LBP_{8,1}$(256) |
| NM | > | > | ≈ | ≈ | > |
| ME | > | > | > | ≈ | > |
| MH | > | > | > | > | > |
| AMD | > | > | ≈ | ≈ | > |

As seen in Table 5, overall, $LBP_{8,1}^{pca}(59)$ achieved the best average performance, $LBP_{8,1}^{pca}(32)$ was the second best, and $LBP_{8,1}^{u2}(59)$ was the third.

For NM, ME, and AMD, most popular descriptors can achieve >0.90 AUC results, but for MH, the AUC was much lower for all (the best was 0.856 from $LBP_{8,1}^{pca}(59)$). In detail, both $LBP_{8,1}^{u2}(59)$ and $LBP_{8,1}^{pca}(59)$ performed significantly better than MS and I for all categories. When compared to O, $LBP_{8,1}^{pca}(59)$ was comparable for NM and AMD, but was significantly better for ME and MH. For MH, $LBP_{8,1}^{pca}(59)$ outperformed O by 5% and by an even larger margin for MS and I. This can be attributed to $LBP_{8,1}^{pca}$'s highly discriminative ability in preserving macular hole structures, which other feature descriptors with smaller neighborhoods do not possess. Also, the use of all 256 bins of LBP histogram gave the worst results, presumably due to overfitting in the high dimensional feature space.

Next, the results of $LBP_{8,1}^{u2}(59)$ and $LBP_{8,1}^{pca}(59)$ were compared. From Tables 4 and 5, these two settings had comparable performance for NM, ME, and AMD, but for MH, $LBP_{8,1}^{pca}(59)$ was significantly better than $LBP_{8,1}^{u2}(59)$. This shows that the removal of individual non-uniform patterns, as used in $LBP_{8,1}^{u2}(59)$, can result in the loss of important discriminative information. Finally, the use of the first 32 principal components ($LBP_{8,1}^{pca}(32)$) was found to be sufficient for NM, ME, and AMD identification. In the remainder of the study, $LBP_{8,1}^{pca}(32)$ was adopted as the local descriptors for all pathologies.

As a next step, global representations were compared. Table 6 compares the performance of a 3-level MSSP with a 3-level spatial pyramid (SP) and a single 2nd-level spatial division (SD) (using only 4×4=16 spatial blocks derived from the original image), all with and without the overlapped blocks ("without" denoted as "\O"):

TABLE 7

(AUC results of different feature types using $LBP_{8,1}^{pca}(32)$ as local descriptor)

| AUC | T | S | TS | Sig. Test |
|---|---|---|---|---|
| NM | 0.969 ± 0.002 | 0.971 ± 0.002 (t = 0.4) | *0.976* ± 0.002 (t = 0.4) | T ≈ S, TS > T, TS ≈ S |
| ME | *0.939* ± 0.004 | 0.923 ± 0.005 (t = 0.3) | *0.939* ± 0.004 (t = 0.4) | T > S, TS ≈ T, TS > S |
| MH | 0.846 ± 0.011 | *0.931* ± 0.005 (t = 0.3) | 0.919 ± 0.005 (t = 0.4) | S > T, TS > T, TS ≈ S |
| AMD | 0.925 ± 0.008 | 0.931 ± 0.005 (t = 0.2) | *0.938* ± 0.006 (t = 0.2) | T ≈ S≈ TS |
| Ave. | 0.920 | 0.939 | *0.943* | |

For NM, ME, MH, and AMD, the best AUCs were 0.976, 0.939, 0.931, and 0.938, derived from the feature type setting: TS (t=0.4), T, S (t=0.4), and TS (t=0.2), respectively. From Table 7, it can be seen that for NM, TS significantly outperformed T though the absolute gain was small (0.7% in AUC); thus, including shape features can provide additional useful information. For ME, T and TS were significantly better than using S alone (1.6% AUC difference), but TS did not outperform T; this suggests that texture descriptors alone, which describe the distribution of intensity patterns, are discriminative enough for edema detection, e.g., detection of dark cystic areas embedded in lighter retinal layers. For MH, S was significantly better than using T or TS, with a large AUC difference (8.5%) between S and T. This reveals that using shape features alone is sufficient to capture the distinct contours of MH, while the details present in texture features might distract the classifier and harm the performance. For

TABLE 6

(AUC results of employing different global frameworks)

| AUC | MSSP | SP | SD | MSSP\O | SP\O | SD\O | Sig. Test |
|---|---|---|---|---|---|---|---|
| NM | *0.969* ± 0.002 | 0.963 ± 0.003 | 0.965 ± 0.002 | 0.963 ± 0.002 | 0.957 ± 0.004 | 0.961 ± 0.003 | MSSP ≈ SP, SD |
| ME | 0.938 ± 0.003 | 0.930 ± 0.005 | 0.927 ± 0.004 | *0.942* ± 0.001 | 0.933 ± 0.005 | 0.930 ± 0.003 | MSSP ≈ SP, SD |
| MH | *0.846* ± 0.011 | 0.817 ± 0.013 | 0.825 ± 0.010 | 0.839 ± 0.015 | 0.804 ± 0.014 | 0.814 ± 0.012 | MSSP > SP, SD |
| AMD | *0.926* ± 0.009 | 0.903 ± 0.007 | 0.908 ± 0.007 | 0.911 ± 0.009 | 0.872 ± 0.011 | 0.866 ± 0.014 | MSSP > SP, SD |
| Ave. | *0.920* | 0.903 | 0.906 | 0.913 | 0.892 | 0.893 | |

In Table 6, only the texture properties from the retinal image were encoded. Significance test results in the last column were based on DeLong test at p=0.05 level.

Overall, the proposed MSSP achieved the best performance. In the MH and AMD categories, MSSP outperformed SP and SL by a large margin, which clearly shows the benefit of multi-scale modeling. When features from the overlapped blocks were removed ("\O"), the performance of all frameworks were considerably lower for AMD and MH, which demonstrates the advantage of including the overlapped blocks.

Figure 11:
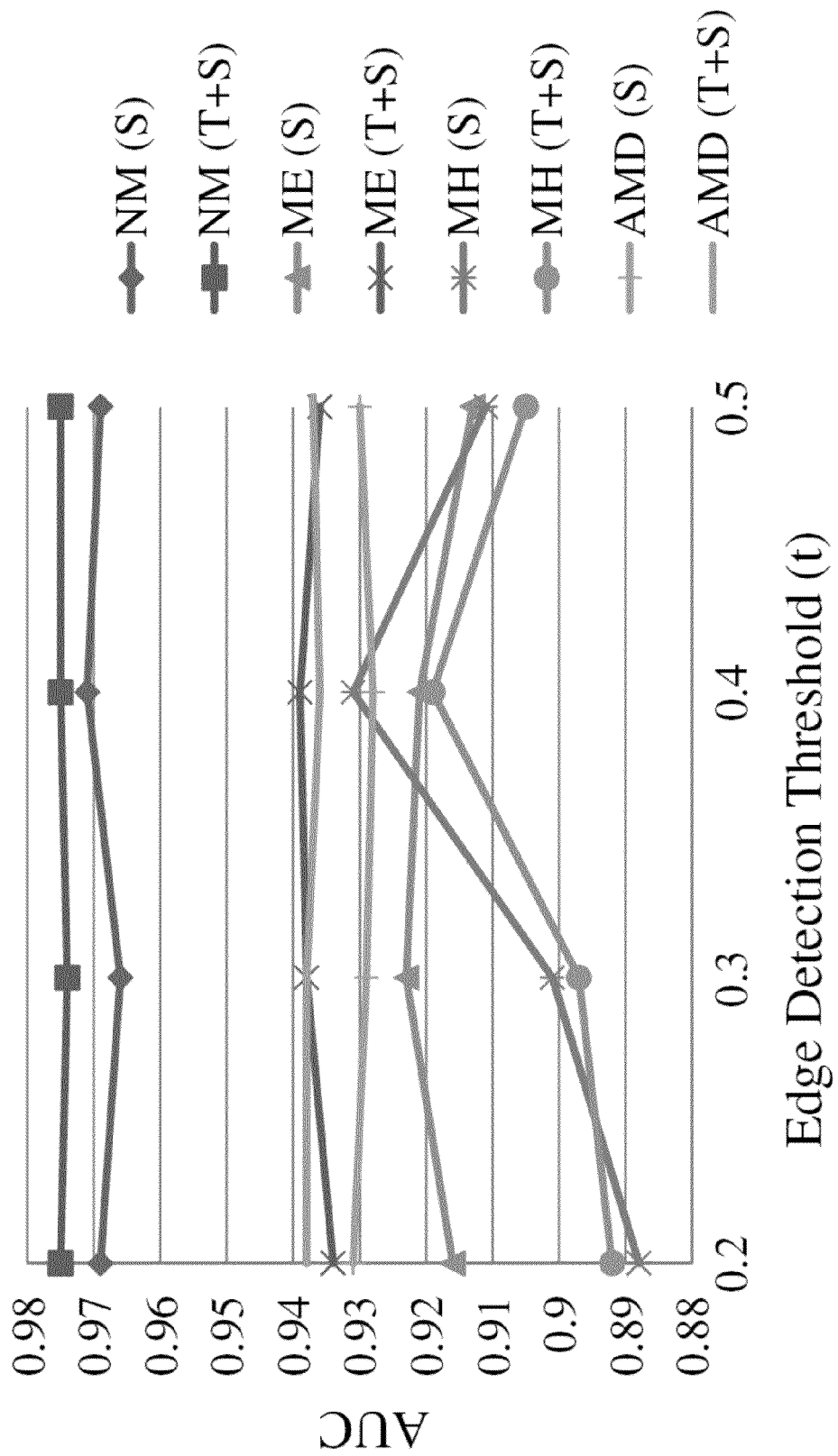
FIG. 11 shows the area under receiver operating characteristic curve (AUC) results under different edge detection thresholds.

Then, the performance of different feature types were evaluated-texture (T) alone, shape (S) alone, or both in combination (TS). For shape features, the performance of several edge detection thresholds (t=0.2, 0.3, ..., 0.5) were tested. FIG. 11 shows the AUC results under different edge detection thresholds t for S and TS, which shows that MH was more sensitive to the setting of t than other categories were. The best AUC results achieved by each feature type are detailed in Table 7:

AMD, all three feature settings (T, S, TS) had no significant difference, but using combined features (TS) achieved the best performance, suggesting that both features types are beneficial.

Regarding the effects of edge detection thresholds t, in FIG. 11, it can be seen that for NM, ME, and AMD, the AUC results under different t were all within 1% in AUC; but for MH, the performance was much more sensitive to the choice of t. In MH, an apparent peak can be seen at t=0.4, which retains relatively strong edges only, as can be seen in FIG. 8. When more weak edges were also included for MH (t<0.4), the performance dropped by a large margin (from 0.931 to 0.888 when t decreased from 0.4 to 0.2). This suggests that including weak edges can be harmful for identifying the hole structures.

Additionally, the experiment evaluated the performance of the techniques discussed herein in discriminating the sub-categories, full-thickness holes (FH) and psedu-holes (PH), within the MH category. The dataset statistics are listed in Table 8:

TABLE 8

(The number of scans, eyes, and subjects for FH and PH, per one expert)

| Statistics | FH | PH |
|---|---|---|
| Scan | 39 | 35 |
| Eye | 17 | 15 |
| Subject | 17 | 18 |

Figure 12:
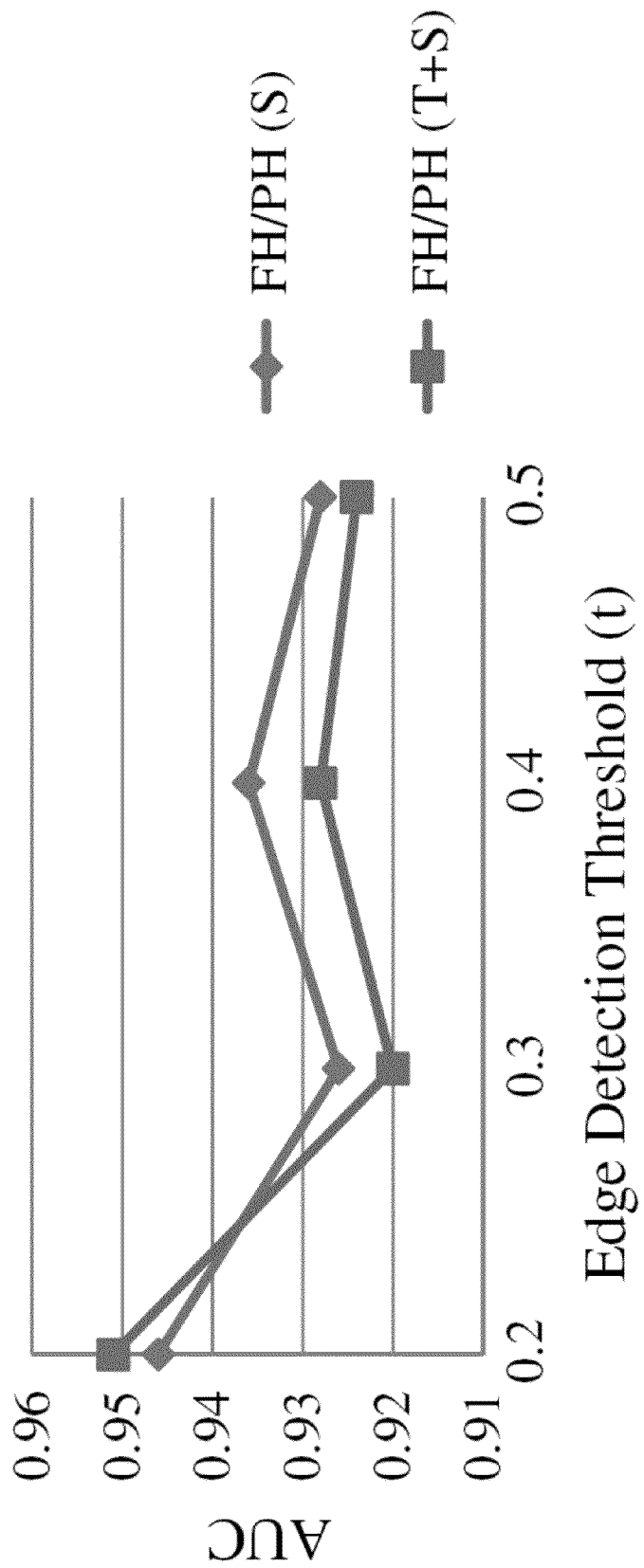
FIG. 12 shows AUC results under varied edge detection thresholds t for classifying between full hole (FH) and pseudohole (PH) categories of MH.

FIG. 12 shows AUC results under varied edge detection thresholds t for classifying between FH and PH categories of MH. The best results for each feature type (T, S, TS) are detailed in Table 9:

TABLE 9

(AUC results in discriminating FH and PH in the MH category with $LBP_{8,r}^{pca}(32)$)

| AUC | T | S | TS | Sig. Test |
|---|---|---|---|---|
| FH vs. PH | 0.871 ± 0.015 | 0.946 ± 0.011 (t = 0.2) | *0.951* ± 0.011 (t = 0.2) | S > T, TS > T, S ≈ TS |

In Table 9, it can be seen that S and TS performed significantly better than T (>7% difference) while S and TS had no significant differences. Again, for distinguishing different hole structures, shape features are much more effective than textures, the same as in the parent category (MH). Regarding the edge detection thresholds t, in FIG. 12, it can be seen that there is a local peak at t=0.4, the same as in the MH category, but when t decreases to 0.2, the inclusion of weaker edges can provide a performance leap. This suggests that subtle shape structures captured by these weak edges are useful for sub-category discrimination. Overall, the high AUC results (0.951) demonstrate that the proposed feature representation is also effective at distinguishing similar-looking subtypes.

Figure 13:
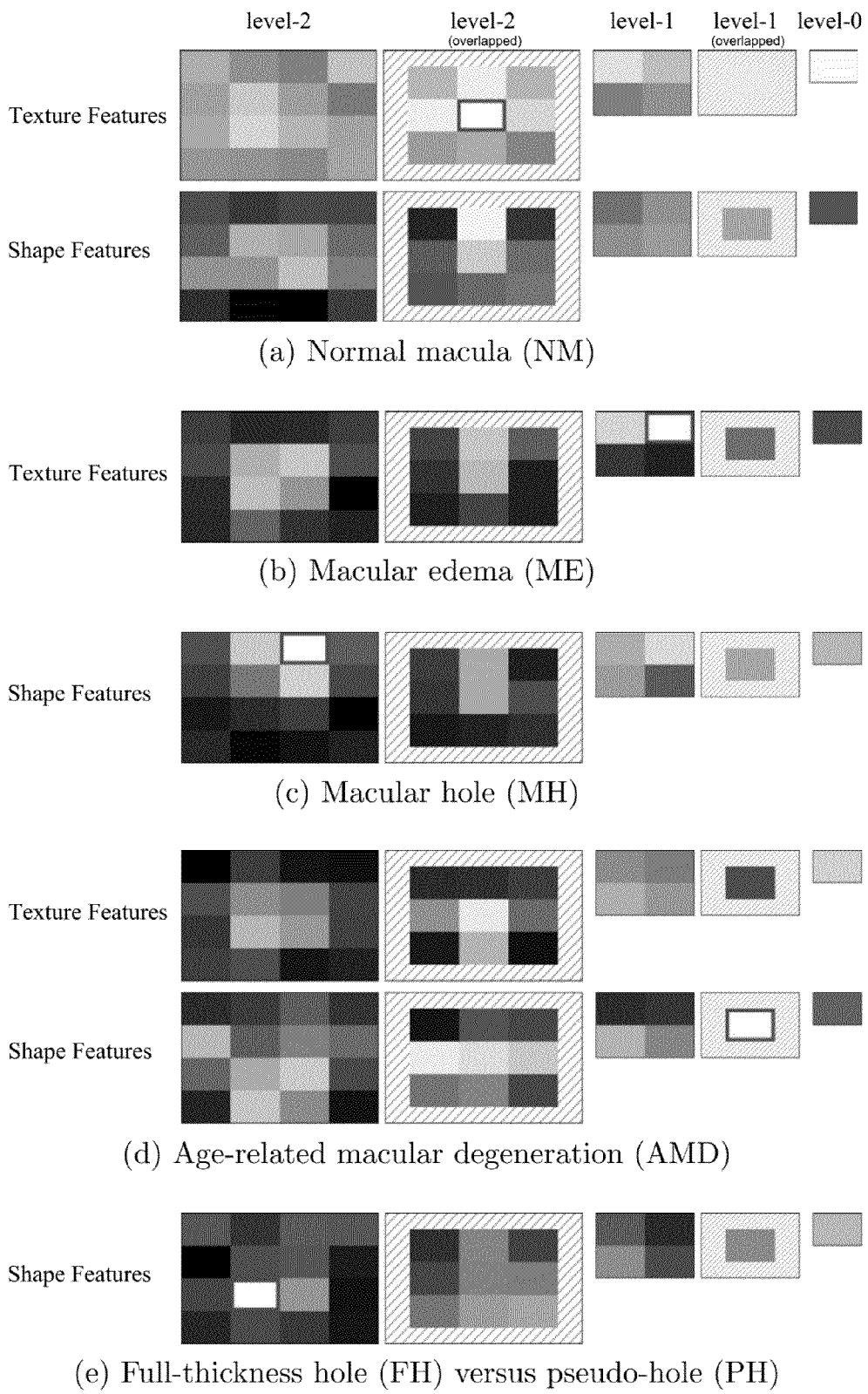
FIG. 13 shows results visualizing the spatial distribution of the most discriminative features of the learned classifiers.

FIG. 13 shows results visualizing the spatial distribution of the most discriminative features of the learned classifiers (e.g., SVMs, etc.). The process and visualization scheme was as follows. For each pathology, a linear SVM was trained using one fold of the training data and the best feature setting (however, other types of classifiers can be used. Examples of classifiers and classification algorithms can include but are not limited to: linear classifiers, Fisher's linear discriminant, logistic regression, naïve Bayes classifier, perceptron, quadratic classifiers, kernel estimation, k-nearest neighbor, boosting, decision trees, random forests, neural networks, Bayesian networks, hidden Markov models, learning vector quantization, etc.). After training, the weight value for each feature entry was derived. Then, for each spatial block, the block's weight was computed by summing up the absolute values of weights from features belonging to the block. For better visualization, the highest block weight was then mapped to 255, and the lowest to 0. The brightest block, which was deemed the most discriminative, is enclosed by a red rectangle.

From FIG. 13, it can be seen that the most discriminative blocks are located at different pyramid levels for different pathologies. Also, for NM and ME, the brighter blocks are located around the central and top areas, which are the places for the normal, smooth depression or the hill shapes caused by the accumulated fluids. For MH, the top half areas, inhabited by the opening area of the holes, get higher weights. For AMD, the middle and bottom areas are brighter, corresponding to the normal or irregular bottom retinal layer (RPE layer). For FH/PH, the area around the central bottom retinal layer, which is the place revealing whether the hole touches the outermost layer, is heavily weighted.

The distribution of these feature weights is consistent with the discussion herein about the important areas for each pathology. The visualization experiment shown in FIG. 13 indicates that a classifier (e.g., SVM, etc.) has the ability to discover the most discriminative features when given the full context, without the need for explicit feature selection beforehand.

In a further study, Dataset A, consisting of 326 macular SD-OCT scans from 136 subjects (193 eyes), was used for deriving the best algorithmic and parameter settings by cross-validation, while Dataset B, containing another 131 macular SD-OCT scans from 37 subjects (58 eyes) collected after the method development stage, was used for testing the performance on novel images.

Since the OCT manufacturer's recommended signal strength (SS) was 8 or above in 1-10 scale, all of the images enrolled in the datasets were qualified SS≥8 criteria. The original scan density was either 200×200×1024 or 512×128×1024 samplings in 6×6×2 mm volumes. All horizontal cross-section images were rescaled to 200×200 for computational efficiency. For each of the scans, the horizontal cross section through the foveal center was then manually selected by one expert ophthalmologist, and this image served as the basis for analysis in this study.

A group of OCT experts masked to any clinical information independently identified the presence or absence of normal macula and each of MH, ME and AMD in the fovea-centered frame. Note that a combination of pathologies can coexist in one cross section. For MH category, both macular hole and macular pseudohole were included in order to simplify the discrimination of all "hole-like" structures from the other cases. Dedicated labeling software was developed where only the pre-selected fovea-centered frame was presented in a randomized order.

For dataset A, three OCT experts gave the pathology labels for each scan, and the majority opinion of the three experts was identified for each pathology and used as the "ground truth" in the method development stage. For dataset B, two of the three experts provided the labels for each scan. For each pathology, the scans with consistent labels were selected for performance evaluation while the scans with different labels were excluded.

The second study's automated method encoded the appearance properties of the retinal images directly, by constructing a global image descriptor based on spatially-distributed multi-scale texture and shape features, combined with machine learning techniques to automatically learn the classifiers for identifying each pathology from a large expert labeled training set.

The study incorporated the shape property of the retinal images in addition to the texture. The analytical method of the further study consisted of the three main steps illustrated in FIG. 5. First, image alignment was performed to remove the curvature and center the image in order to reduce the appearance variation across scans. Second, a global image descriptor was constructed from the aligned image and its derived edge image (Canny, etc.). Multi-scale spatial pyramid (MSSP) was used as the global representation for capturing the spatial organization of the retina in multiple scales and spatial granularities, although other (multi-scale) or non-multi-scale spatial divisions can be used. To encode each local block, the dimension-reduced local binary pattern (LBP) histogram based on principle component analysis (PCA) was used as the local block descriptor. The local features derived from each spatial block in the multiple rescaled images and their edge images were concatenated in a fixed order to form the overall global descriptor. These histogram-based local features of the image and the edge map were utilized to encode the texture and shape characteristics of the retinal image, respectively. Finally, for each pathology, a two-class non-linear support vector machine (SVM) classifier with radial basis function (RBF) kernel and estimated probability values was trained using the image descriptors and their labels from the training set (however, other classifiers can be used, as described herein).

The method was developed on dataset A as described above in the first study. After performing detailed analysis on dataset A, the best algorithmic settings and parameters determined for identifying each pathology were then applied to the test dataset B. The performance on dataset B was thus representative for the generalization ability of the proposed approach. For MH category, dataset B did not contain macular hole cases (which coincides with real clinical situations, since macular hole has low occurrence (approximately 3.3 cases in 1000 in those persons older than 55 years)). To deal with this situation, for MH performance testing only, the training and testing dataset was reorganized such that 80% of MH cases originated from dataset A were randomly sampled and included in the training set and the rest were included in the testing set.

The characteristics of Dataset A were as described above in connection with the first study. Again the majority opinion of the image labeling was used as the ground truth so that the standard was not biased towards any specific expert.

Figure 14:
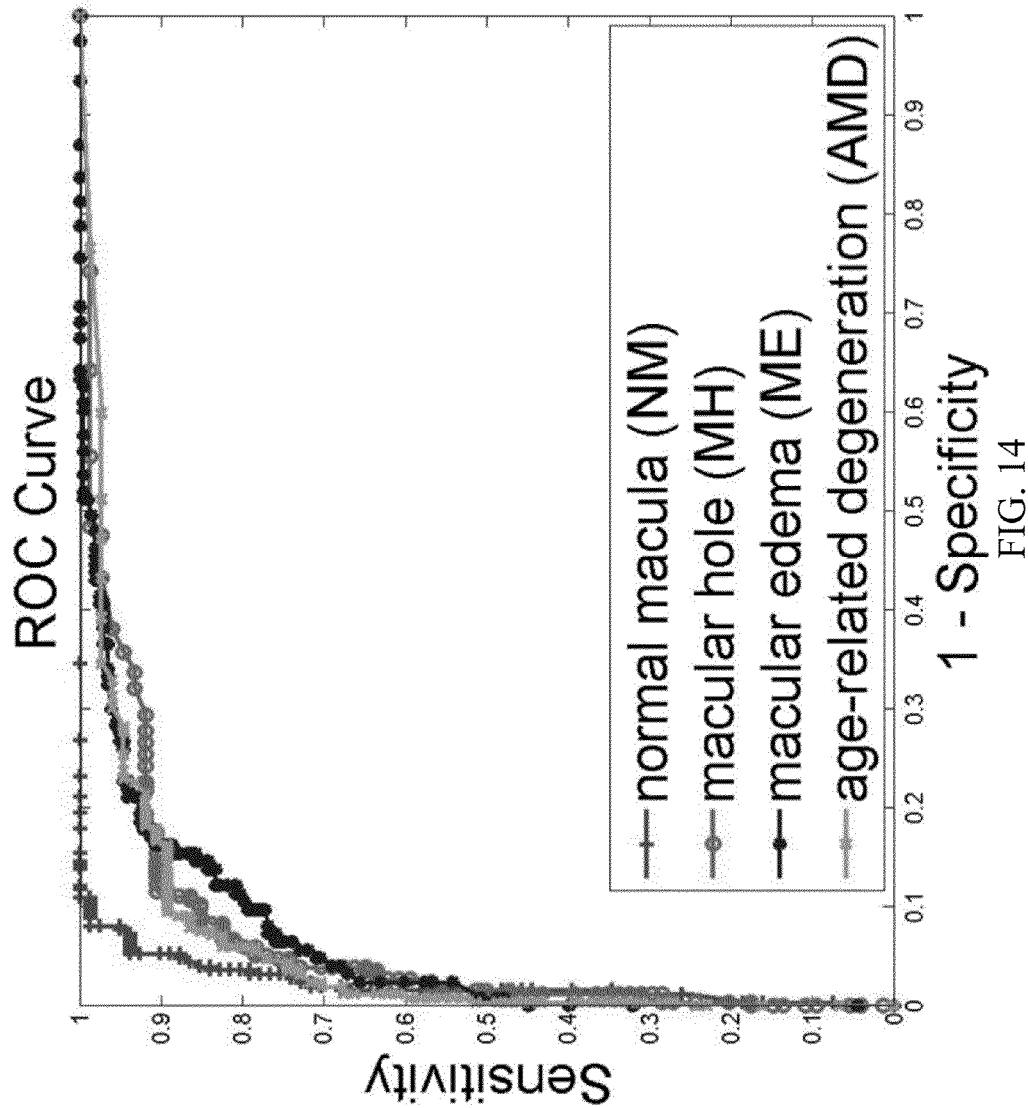
FIG. 14 illustrates the receiver operating characteristic (ROC) curves generated from one of six random data splits.

As explained, different feature settings—texture (T) alone, shape (S) alone, and in combination (TS)—were tested on dataset A, so that the discriminative power of each feature type for each pathology could be evaluated. For shape features, the edge detection threshold, denoted as t, was tested at various values so that different quantities of edges were obtained and encoded. The AUCs for the different feature settings were reported in Table 7, above. The best AUCs for NM, MH, ME, and AMD, were 0.976, 0.931, 0.939, and 0.938, derived from the setting: TS(t=0.4), S(t=0.4), TS(t=0.4), and TS(t=0.2), respectively. FIG. 14 illustrates the ROC curves generated from one of six random data splits.

Regarding the edge detection thresholds t for shape features, it was discovered that for NM, ME, and AMD, the AUC results under different t settings were all within 1% in AUC; but for MH, the performance was much more sensitive to the choice of t (AUC was 0.888, 0.901, 0.931, and 0.911 when t varied from 0.2 to 0.5) with the best performance at t=0.4; this suggests that for MH, encoding the stronger edges is more helpful in identifying the hole structures; the weaker edges (t=0.2) might add noises instead and distract the classifiers.

The statistical significance of the performance difference under different feature settings was also evaluated. It was found that for NM, TS outperformed T though the absolute gain was small (0.7% in AUC); thus, including shape features can provide additional useful information. For MH, S was significantly better than using T and TS, with a large AUC difference (8.5%) between S and T; this reveals that using shape feature alone is sufficient to capture the distinct contours of MH. For ME, T and TS was significantly better than using S (1.6% AUC difference), but TS and T has similar performance; this suggests that encoding the intensity patterns (textures) is more informative than just describing the shapes. For AMD, all three feature settings (T, S, TS) had no significant difference, but using combined features (TS) achieved the best AUC performance, suggesting that both feature types are useful.

In implementation, for NM, ME, and AMD, the feature vectors were computed from the aligned retinal image directly, which was 200 pixels in width; for MH, the features were extracted from the further down-sized image (rescaled to 100 pixels in width). This rescaling for MH improved the performance by 3% consistently under different feature type settings. This suggests that removing the details or noises residing in the original resolution can help identification of the hole structures.

To compare the labeling performance of the automated method to that of each expert against the majority-based ground truth, the balanced accuracy (average of sensitivity and specificity) of the automated method and each expert was computed. For the automated method, the best balanced accuracy was derived from the ROC curve. The results were detailed in Table 10:

TABLE 10

(Balanced accuracy of each expert and the automated method against ground truth)

| B. Accuracy | Expert 1 | Expert 2 | Expert 3 | Auto. method |
|---|---|---|---|---|
| NM | 99.8 | 98.4 | 99.4 | 95.5 |
|  | (100, 99.6) | (98.8, 98.0) | (100, 98.8) | (99.4, 91.5) |
| MH | 99.4 | 98.3 | 86.5 | 89.7 |
|  | (100, 98.8) | (98.6, 98.0) | (73.0, 100) | (89.1, 90.3) |
| ME | 92.4 | 94.9 | 91.7 | 87.3 |
|  | (99.5, 85.4) | (94.6, 95.1) | (89.2, 94.3) | (87.5, 87.0) |
| AMD | 94.2 | 94.0 | 92.0 | 89.3 |
|  | (93.2, 95.2) | (89.2, 98.8) | (85.1, 98.8) | (89.7, 88.8) |
| Average | 96.5 | 96.4 | 92.4 | 90.5 |
|  | (98.2, 94.8) | (95.3, 97.5) | (86.8, 98.0) | (91.4, 89.4) |

In each cell of Table 10, the balanced accuracy is listed along with the corresponding sensitivity and specificity values in parentheses. For the automated method, the best feature setting for each pathology was adopted (TS(t=0.4), S(t=0.4), TS, TS(t=0.2) for normal macula (NM), macular hole (MH), macular edema (ME), age-related macular degeneration (AMD), respectively); the best balanced accuracy was derived from the mean of the output of the 6 runs.

Overall, the automated analysis method achieved good balanced accuracy for NM (95.5%), but relatively lower performance for MH, ME, and AMD (89.7%, 87.3%, and 89.3%). The automated software was inferior to the experts in most cases, but when compared to expert 3 the performance differences were all within 5% for all categories (the difference is −3.9%, +3.2%, −4.4%, −2.7% for NM, MH, ME, and AMD, respectively).

Figure 15:
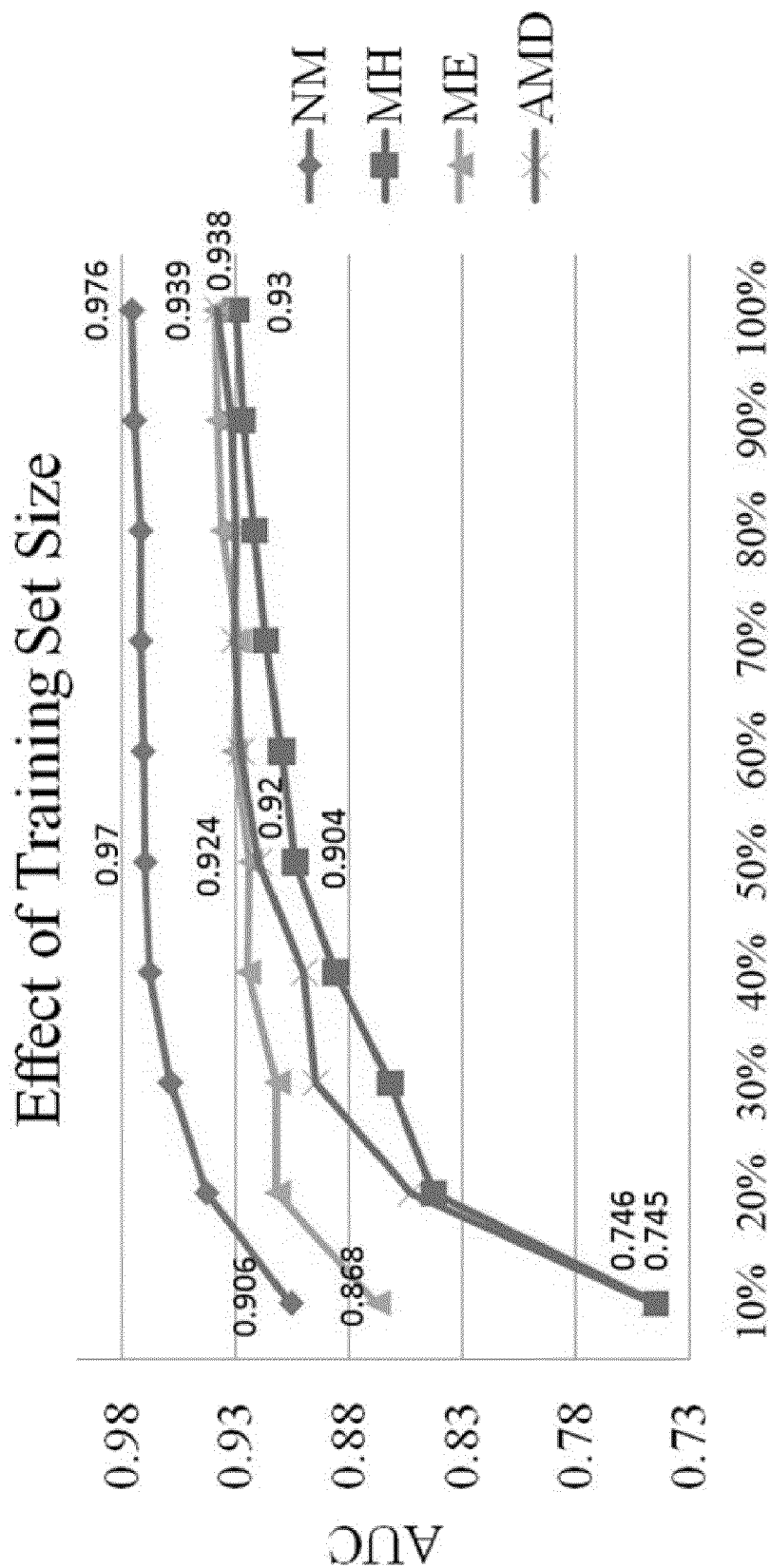
FIG. 15 illustrates the results of sampling varying percentages of positive and negative subjects from a training dataset.

The AUC performances of the automated method with respect to varied training size on dataset A were also studied. The ten-fold cross-validation setting was still used, but for each training fold, k % of positive and negative subjects were sampled and utilized for training, while the testing fold remained the same. FIG. 15 illustrates the results of sampling k % of positive and negative subjects from dataset A for training, with settings of k=10, 20, . . . , 100. The AUC results of 10%, 50%, and 100% training set were 0.906. 0.970, 0.976 for NM, 0.745, 0.904, 0.931 for MH, 0.868, 0.924, 0.939 for ME, and 0.746, 0.920, 0.938 for AMD. These results showed that using more training data can improve the performance in all categories. For MH, a larger gain (2.7%) and clearer increasing trend from 50% to 100% can be observed, suggesting that adding more training instances for MH can improve the performance the most.

In order to understand the influence of cases where there is inconsistent labeling, an experiment using only images with complete labeling agreement for each pathology separately was also conducted. In this setting, 316 (96.9%), 297 (91.1%), 261 (80.1%), 284 (87.1%) images from original 326 images were selected for NM, MH, ME, and AMD identification, respectively (as illustrated in the Venn diagram in FIG. 9). The AUC results are listed in Table 11:

TABLE 11

(AUC results of using the entire dataset A vs. only images of complete consensus)

| AUC on Dataset A | NM | MH | ME | AMD |
|---|---|---|---|---|
| All images (326 scans) | 0.976 | 0.931 | 0.939 | 0.938 |
| Images of Complete Consensus from 3 Experts (316, 297, 261, 284 scans) | 0.984 | 0.932 | 0.985 | 0.968 |

As seen in Table 11, when using only images with complete consensus, the performance for NM and MH is slightly enhanced (~1%) but it is much better for ME (from 0.939 to 0.985) and AMD (from 0.938 to 0.968). This suggests that the larger ambiguity in ME and AMD identification, as noted in the lower Kappa values in table 2, is a factor in influencing the performance of the automated method.

To test the performance on the hold-out dataset B, the pathology classifiers were trained using the images from dataset A, with the best algorithmic settings determined in analyzing dataset A (TS(t=0.4), S(t=0.4), TS(t=0.4), and TS(t=0.2) for NM, MH, ME, and AMD, respectively) per the first study. For this experiment, the ground truth was defined by the consensus between the same two experts for both datasets. The consensus includes 96.9%, 95.4%, 88.0%, and 90.5% of 326 scans from dataset A for training, and 94.7%, 100%, 90.0%, and 84.7% of 131 scans from dataset B for testing, for NM, MH, ME, and AMD, respectively. The pathology distribution for both datasets is detailed in Table 12:

TABLE 12

(positive scans, eyes and subjects vs. total cases per the consensus of experts 1 and 2)

|  | NM | MH* | ME | AMD |
|---|---|---|---|---|
| Training Statistics |  |  |  |  |
| Scan | 80/316 | 49/287 | 190/287 | 59/295 |
| Eye | 66/187 | 27/176 | 109/180 | 27/178 |
| Subject | 65/133 | 26/128 | 84/130 | 21/133 |
| Testing Statistics |  |  |  |  |
| Scan | 22/124 | 21/153 | 59/118 | 81/111 |
| Eye | 13/54 | 8/66 | 29/54 | 31/50 |
| Subject | 10/36 | 6/43 | 23/34 | 20/33 |

Figure 16:
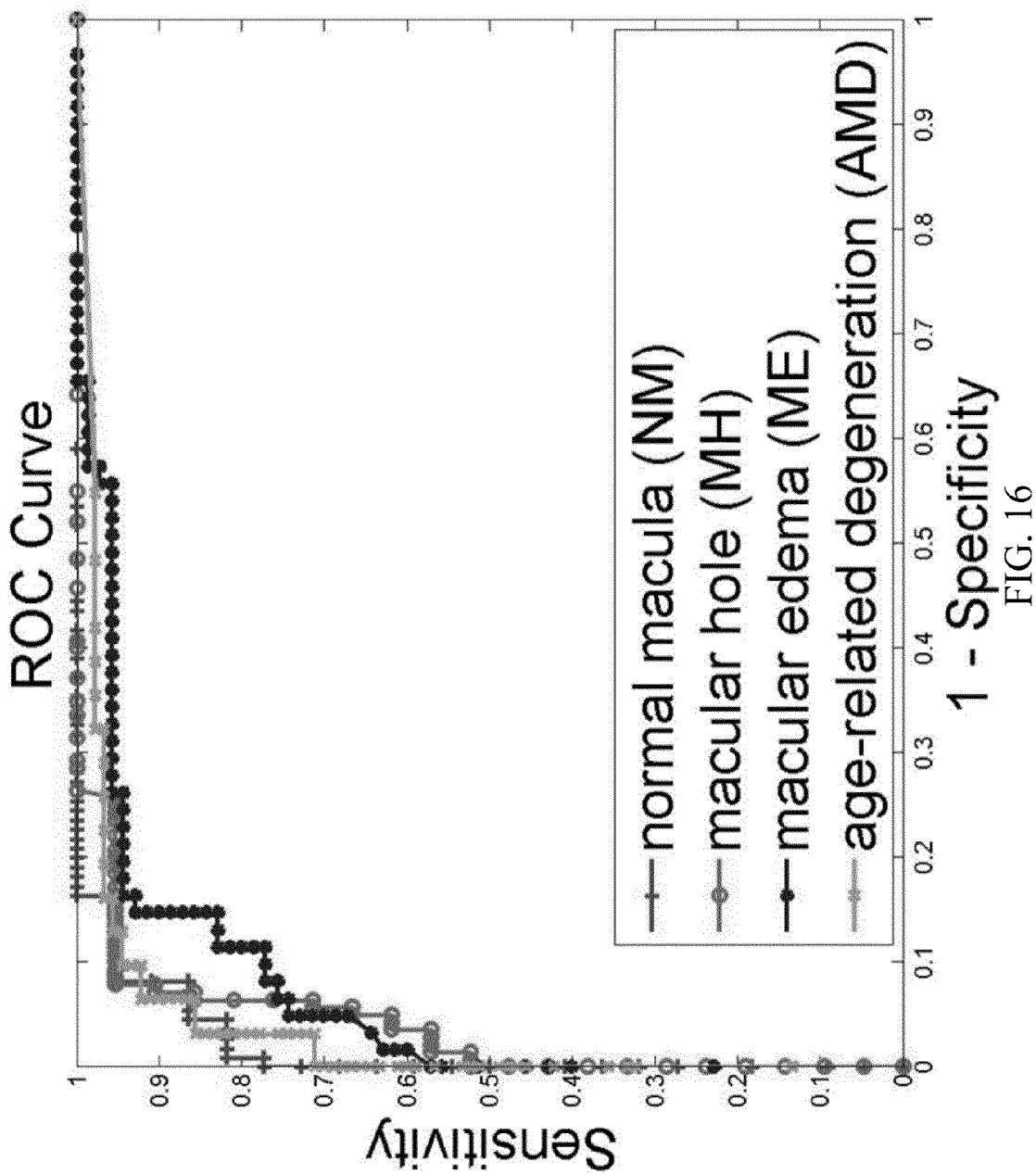
FIG. 16 illustrates the ROC curve of testing on a testing dataset, based on the pathology classifiers trained using images from a training dataset.

FIG. 16 illustrates the ROC curve of testing on dataset B, based on the pathology classifiers trained using images from dataset A. The ground truth for this experiment was defined by the consensus of the two experts (expert 1 and 2) on both datasets. The statistics of pathology distribution is listed above in Table 12. The feature and parameter setting for each pathology were determined using dataset A only: TS (t=0.4), S (t=0.4), TS, and TS (t=0.2) for normal macula (NM), macular hole (MH), macular edema (ME), and age-related macular degeneration (AMD), respectively. The AUC results corresponding to FIG. 16 are shown in Table 13:

TABLE 13

(AUC and best balanced accuracy on dataset B, as trained using dataset A)

| Performance on Dataset B | NM | MH | ME | AMD |
|---|---|---|---|---|
| AUC | 0.978 | 0.969 | 0.941 | 0.975 |
| Best B. Accuracy | 95.5% | 97.3% | 90.5% | 95.2% |

In

The AUC is 0.978, 0.969, 0.941, and 0.975, and the best balanced accuracy is 95.5%, 97.3%, 90.5%, and 95.2% for NM, MH, ME, and AMD, respectively. The AUC performance on all pathologies are good (AUC>0.94) and comparable to the cross-validation AUC results on the training dataset A (AUC>0.93). These results suggest that the techniques discussed herein can be effective in identifying pathologies for future unseen images.

In the second study, a machine-learning based approach was used to identify the presence of normal macula and several macular pathologies, MH, ME, and AMD, from a fovea-centered cross section in a macular SD-OCT scan. A large dataset (dataset A) containing 326 scans from 136 subjects with healthy macula or assorted macular pathologies was used for developing the methodology, and a separate dataset (dataset B), with 131 scans from 37 subjects, was used as a hold-out testing set.

On the developing dataset (dataset A), the automated analysis achieved >0.93 AUC results for all macular pathologies using 10-fold cross-validation, with particularly good performance on identifying the normal macula (AUC=0.976). This can be attributed to the reduced variation in normal appearance across scans. For pathology identification, the performance reduced somewhat, likely due to the greater within-category appearance variations, lack of sufficient training data especially for MH and AMD, and the ambiguity existing in the majority-opinion based ground truth as shown in the kappa agreement analysis between the experts, but still remained quite high.

By analyzing the performance on dataset A, the discriminative power of using texture or shape features alone as well as their combination was studied. Under DeLong test, for MH the use of shape features is more effective than texture features, while for ME texture features outperforms shapes. This makes sense since macular holes are marked by the distinct contours of holes while detection of edema requires intensity comparison information, e.g., dark cystic areas embedded in the lighter retinal layers. For NM and AMD, the combined features achieved the highest AUC results, but this setting did not significantly outperform using either feature alone. However, as more images are made available for a larger training set (as, for example, in some embodiments discussed herein for continued expansion of training sets, e.g., via updates), utilizing all complimentary features can result in superior performance, since the over-fitting phenomenon in the high dimensional feature space can be mitigated and the true discriminative information can be more effectively represented.

The AUC results with respect to varied training set size (10%, 20%, . . . , 100%) show that exploiting more training data can consistently enhance the performance in all categories, especially for MH. Training on additional MH cases can boost the performance the most.

To show the influence of inconsistent labeling in the majority-opinion based ground truth from dataset A, the AUC results from using only images with complete consensus for each pathology were studied. The much higher AUC results for ME and AMD (0.985 and 0.968, respectively) indicated potential advantages when the two classes (presence and absence) can be well separated. However, in reality, there are always subtle cases residing in the gray area in between, causing ambiguity in dichotomy labeling. Refined labeling (e.g., by "pathological degree" ("absent", "early" or "advanced")) can potentially result in improved labeling consistency and superior performance in automated software. However, for improved performance, a larger amount of training data in discriminating different pathological stages may be a consideration.

The method discussed in these studies achieved good AUC results (>0.94 for all pathology categories) on the hold-out testing set (dataset B), when using images from the developing dataset (dataset A) for classifier training. This indicates its usefulness in classifying future unseen images.

The proposed method has several advantages. First, our histogram-based image features directly capture the statistical distribution of appearance characteristics, resulting in objective measurements and straightforward implementation. Second, our method is not limited to any one pathology and can be applied to identify additional pathologies. Third, the same approach can be utilized to examine other cross sections besides the foveal slice, as long as the labeled cross-sections from the desired anatomical location are also collected for training.

Although the studies focused only on fovea-centered slices, in aspects of the subject innovation, every slice in the 3D scan data can be examined so that any abnormality can be identified, even when no pathology is observed at the fovea-centered frame (an unlikely event).

The slice diagnosis method of the studies can be extended to analyze each slice in the entire cube, once the pathology labeling for each cross section can be gathered. One way this can be accomplished is by training a set of y-location indexed pathology classifiers using the labeled slice set from the same quantized y location relative to the fovea. By using location-specific classifiers, the normal and abnormal anatomical structures around similar y locations can be modeled more accurately and the entire volume can be examined. Additionally, if eye motion artifacts in the macular scans are corrected for, the techniques discussed herein can be employed in connection with volumetric features for pathology identification. Additionally, other features of the subject innovation can benefit from the automated (e.g., via classifiers such as SVMs, etc.) techniques discussed herein. For example, fovea localization can be automated by training with a training set of OCT scans with expert-located fovea-centered slices (in both healthy and pathological tissue), to train recognition of features corresponding to fovea-centered slices. In this way, selection of slices can be automated.

Figure 17:
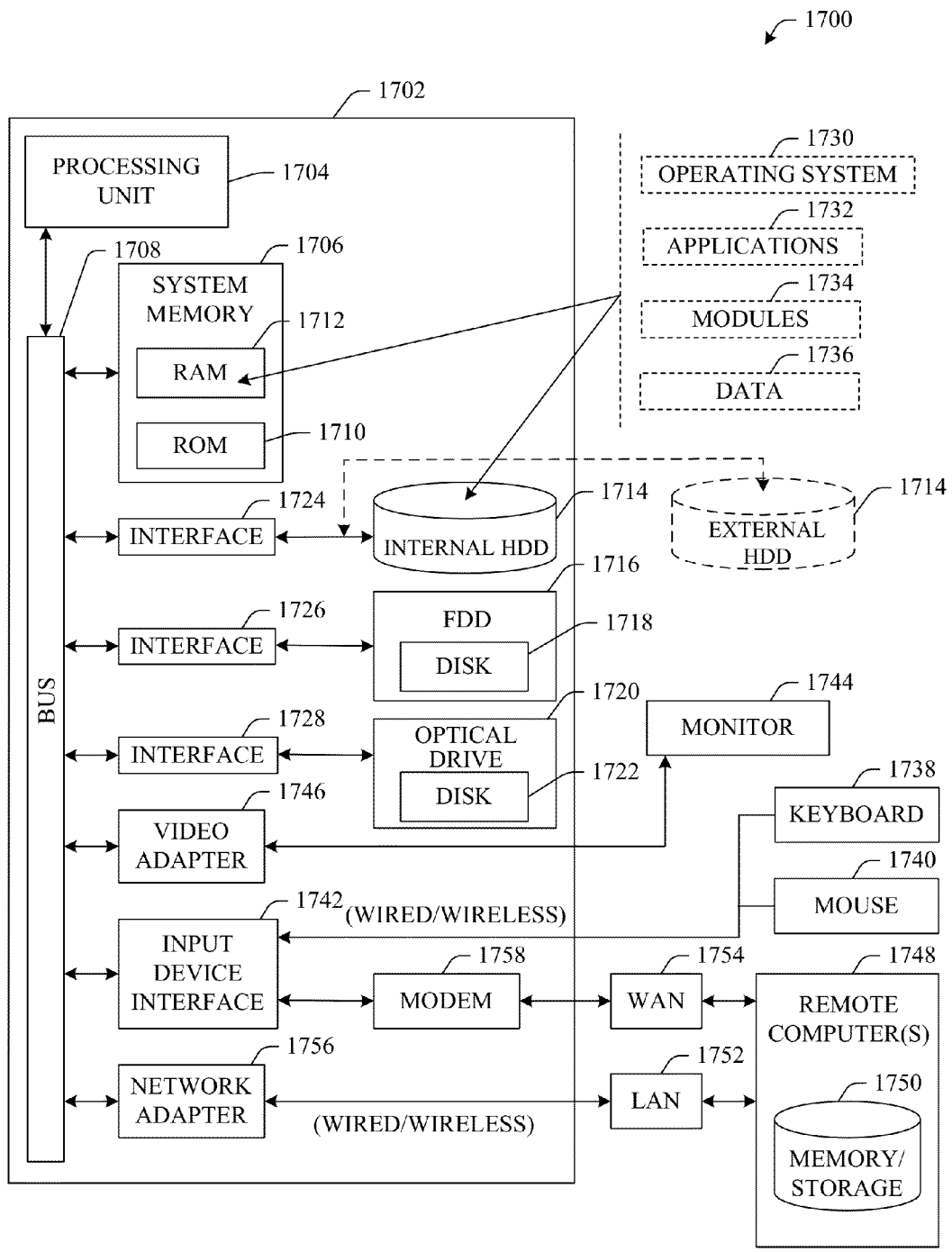
FIG. 17 illustrates a block diagram of a computer operable to execute the disclosed architecture.

Referring now to FIG. 17, there is illustrated a block diagram of a computer operable to execute the disclosed architecture. In order to provide additional context for various aspects of the subject innovation, FIG. 17 and the following discussion are intended to provide a brief, general description of a suitable computing environment 1700 in which the various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 17, the exemplary environment 1700 for implementing various aspects of the innovation includes a computer 1702, the computer 1702 including a processing unit 1704, a system memory 1706 and a system bus 1708. The system bus 1708 couples system components including, but not limited to, the system memory 1706 to the processing unit 1704. The processing unit 1704 can be any of various commercially available processors. Dual microprocessors and other multi-processor architectures may also be employed as the processing unit 1704.

The system bus 1708 can be any of several types of bus structure that may further interconnect to a memory bus (with or without a memory controller), a peripheral bus, and a local bus using any of a variety of commercially available bus architectures. The system memory 1706 includes read-only memory (ROM) 1710 and random access memory (RAM) 1712. A basic input/output system (BIOS) is stored in a non-volatile memory 1710 such as ROM, EPROM, EEPROM, which BIOS contains the basic routines that help to transfer information between elements within the computer 1702, such as during start-up. The RAM 1712 can also include a high-speed RAM such as static RAM for caching data.

The computer 1702 further includes an internal hard disk drive (HDD) 1714 (e.g., EIDE, SATA), which internal hard disk drive 1714 may also be configured for external use in a suitable chassis (not shown), a magnetic floppy disk drive (FDD) 1716, (e.g., to read from or write to a removable diskette 1718) and an optical disk drive 1720, (e.g., reading a CD-ROM disk 1722 or, to read from or write to other high capacity optical media such as the DVD). The hard disk drive 1714, magnetic disk drive 1716 and optical disk drive 1720 can be connected to the system bus 1708 by a hard disk drive interface 1724, a magnetic disk drive interface 1726 and an optical drive interface 1728, respectively. The interface 1724 for external drive implementations includes at least one or both of Universal Serial Bus (USB) and IEEE 1394 interface technologies. Other external drive connection technologies are within contemplation of the subject innovation.

The drives and their associated computer-readable media provide nonvolatile storage of data, data structures, computer-executable instructions, and so forth. For the computer 1702, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and RAM 1712, including an operating system 1730, one or more application programs 1732, other program modules 1734 and program data 1736. All or portions of the operating system, applications, modules, and/or data can also be cached in the RAM 1712. It is appreciated that the innovation can be implemented with various commercially available operating systems or combinations of operating systems.

A user can enter commands and information into the computer 1702 through one or more wired/wireless input devices, e.g., a keyboard 1738 and a pointing device, such as a mouse 1740. Other input devices (not shown) may include a microphone, an IR remote control, a joystick, a game pad, a stylus pen, touch screen, or the like. These and other input devices are often connected to the processing unit 1704 through an input device interface 1742 that is coupled to the system bus 1708, but can be connected by other interfaces, such as a parallel port, an IEEE 1394 serial port, a game port, a USB port, an IR interface, etc.

A monitor 1744 or other type of display device is also connected to the system bus 1708 via an interface, such as a video adapter 1746. In addition to the monitor 1744, a computer typically includes other peripheral output devices (not shown), such as speakers, printers, etc.

The computer 1702 may operate in a networked environment using logical connections via wired and/or wireless communications to one or more remote computers, such as a remote computer(s) 1748. The remote computer(s) 1748 can be a workstation, a server computer, a router, a personal computer, portable computer, microprocessor-based entertainment appliance, a peer device or other common network node, and typically includes many or all of the elements described relative to the computer 1702, although, for purposes of brevity, only a memory/storage device 1750 is illustrated. The logical connections depicted include wired/wireless connectivity to a local area network (LAN) 1752 and/or larger networks, e.g., a wide area network (WAN) 1754. Such LAN and WAN networking environments are commonplace in offices and companies, and facilitate enterprise-wide computer networks, such as intranets, all of which may connect to a global communications network, e.g., the Internet.

When used in a LAN networking environment, the computer 1702 is connected to the local network 1752 through a wired and/or wireless communication network interface or adapter 1756. The adapter 1756 may facilitate wired or wireless communication to the LAN 1752, which may also include a wireless access point disposed thereon for communicating with the wireless adapter 1756.

When used in a WAN networking environment, the computer 1702 can include a modem 1758, or is connected to a communications server on the WAN 1754, or has other means for establishing communications over the WAN 1754, such as by way of the Internet. The modem 1758, which can be internal or external and a wired or wireless device, is connected to the system bus 1708 via the serial port interface 1742. In a networked environment, program modules depicted relative to the computer 1702, or portions thereof, can be stored in the remote memory/storage device 1750. It will be appreciated that the network connections shown are exemplary and other means of establishing a communications link between the computers can be used.

The computer 1702 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

Figure 18:
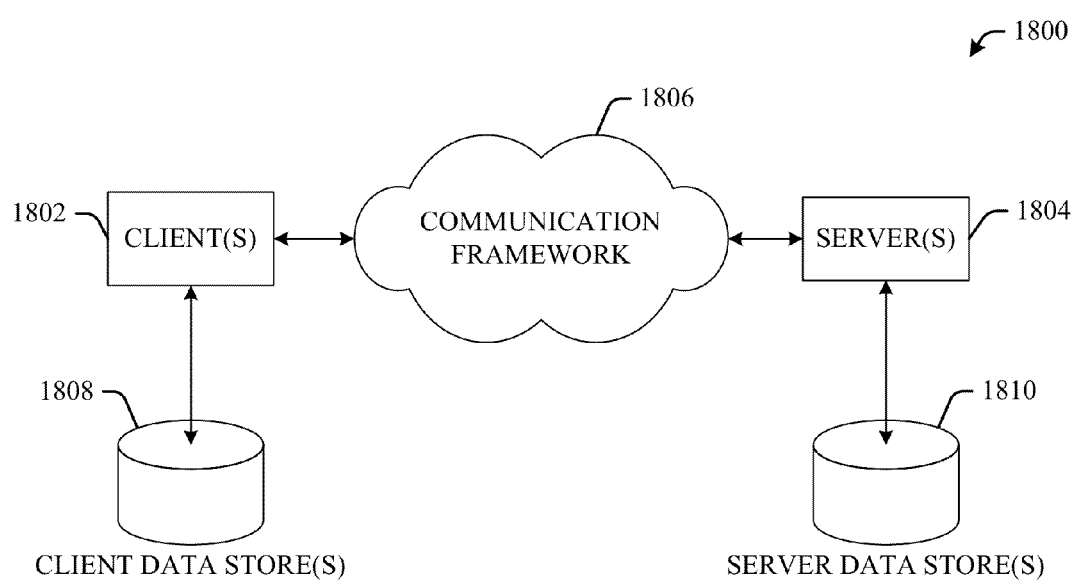
FIG. 18 illustrates a schematic block diagram of an exemplary computing environment in accordance with the subject innovation.

Referring now to FIG. 18, there is illustrated a schematic block diagram of an exemplary computing environment 1800 in accordance with the subject innovation. The system 1800 includes one or more client(s) 1802. The client(s) 1802 can be hardware and/or software (e.g., threads, processes, computing devices). The client(s) 1802 can house cookie(s) and/or associated contextual information by employing the innovation, for example.

The system 1800 also includes one or more server(s) 1804. The server(s) 1804 can also be hardware and/or software (e.g., threads, processes, computing devices). The servers 1804 can house threads to perform transformations by employing the innovation, for example. One possible communication between a client 1802 and a server 1804 can be in the form of a data packet adapted to be transmitted between two or more computer processes. The data packet may include a cookie and/or associated contextual information, for example. The system 1800 includes a communication framework 1806 (e.g., a global communication network such as the Internet) that can be employed to facilitate communications between the client(s) 1802 and the server(s) 1804.

Communications can be facilitated via a wired (including optical fiber) and/or wireless technology. The client(s) 1802 are operatively connected to one or more client data store(s) 1808 that can be employed to store information local to the client(s) 1802 (e.g., cookie(s) and/or associated contextual information). Similarly, the server(s) 1804 are operatively connected to one or more server data store(s) 1802 that can be employed to store information local to the servers 1804.

Moreover, systems and methods discussed herein provide techniques that can automate diagnosis of multiple macular pathologies in retinal OCT images. These techniques (e.g., spatially-distributed multi-scale texture and shape descriptors combined with a data-driven framework, etc.) can effectively identify the discriminative features. Embodiments of the subject innovation can provide clinically useful tools to support disease identification, improving the efficiency of OCT based examination. Additionally, although the results presented herein relate specifically to identifying macular pathologies, the techniques discussed herein can be employed in other settings to automate diagnosis of diseases based on OCT images.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system that facilitates automated diagnosis of diseases, comprising:
   an alignment component that aligns a 2-dimensional (2D) slice of an optical coherence tomography (OCT) image of a retina to produce an aligned slice, wherein the aligned slice comprises an approximately horizontal image of the retina;
   a feature construction component that determines at least one global representation and at least one local descriptor based at least in part on the aligned image, wherein the at least one local descriptor comprises a local binary pattern (LBP)-based feature, wherein the at least one global representation comprises a (multi-scale) spatial division, wherein the (multi-scale) spatial division is a multi-scale spatial pyramid (MSSP);
   a classification component that comprises one or more classifiers, wherein each classifier classifies the aligned image into one of a plurality of categories associated with at least one ocular pathology; and
   a processor configured for executing instructions associated with at least one of the alignment component, the feature construction component, or the classification component.

2. The system of claim 1, wherein the feature construction component constructs an edge map based at least in part on the aligned slice, and wherein the at least one global representation and the at least one local descriptor are based at least in part on one or more of the aligned image or the edge map.

3. The system of claim 1, wherein the alignment component performs one or more of the following acts: the alignment component thresholds the 2D slice, the alignment component applies a filter to remove noise from the 2D slice, the alignment component morphologically opens and closes the slice, the alignment component fits a curve to a found retina of the slice, or the alignment component warps the slice based at least in part on the fit curve.

4. The system of claim 1, wherein the LBP-based feature is based at least in part on a $LBP_{8,1}$.

5. The system of claim 1, wherein the classification component determines the presence or absence of at least one of a normal retina, or the at least one ocular pathology, wherein the at least one ocular pathology is one or more of macular edema (ME), macular hole (MH), or age-related macular degeneration (AMD).

6. The system of claim 5, wherein at least one of the classifiers determines a sub-category associated with one of the at least one ocular pathology.

7. The system of claim 1, further comprising an OCT system that captures the OCT image.

8. The system of claim 1, further comprising a selection component that selects the 2D slice of the OCT image.

9. The system of claim 1, further comprising a database that comprises reference data, wherein the one or more classifiers are trained based on at least a subset of the reference data.

10. The system of claim 1, further comprising an output component that provides at least one probability associated with the at least one ocular pathology.

11. A method of analyzing an optical coherence tomography (OCT) image of a retina, comprising:
    aligning a 2-dimensional (2D) slice of the OCT image to produce an approximately horizontal image of the retina;
    constructing an edge map based at least in part on the aligned 2D slice;
    determining at least one global representation based at least in part on the 2D slice or the edge map, wherein determining the at least one global representation comprises determining a (multi-scale) spatial division, wherein the (multi-scale) spatial division is a multi-scale spatial pyramid (MSSP);
    creating at least one local binary pattern (LBP)-based feature based at least in part on the at least one global representation; and
    classifying the 2D slice into one or more categories via one or more classifiers, wherein each category is associated with at least one ocular pathology, wherein the classifying is based at least in part on the at least one LBP-based feature.

12. The method of claim 11, wherein creating at least one LBP-based feature comprises creating at least one feature based at least in part on $LBP_{8,1}$.

13. The method of claim 11, wherein the aligning further comprises at least one of:
    thresholding the 2D slice to detect a majority of the structure of the retina;
    applying a filter to remove noise from the 2D slice;
    applying morphological operations to find the entire retina;
    fitting a curve to the found retina; or
    warping the found retina based at least in part on the fitted curve.

14. The method of claim 11, wherein the one or more classifiers comprises one or more nonlinear support vector machines (SVMs) based at least in part on radial basis functions (RBFs).

15. The method of claim 11, wherein the classifying comprise determining which of at least two subcategories of an identified ocular pathology is best associated with the aligned image, based at least in part on the at least one LBP-based feature.

16. The method of claim 11, wherein the one or more classifiers comprises at least one 2-class support vector machine (SVM).

17. A method of automated diagnosis of one or more macular pathologies, comprising:
   aligning an optical coherence tomography (OCT) image of a retina, comprising at least one of:
      detecting a majority of the retina structures by thresholding the image;
      removing noise from the image by applying a median filter;
      using morphological closing and opening to find an entire image of the retina;
      using a least-square curve fitting to fit a curve to the entire image of the retina; or
      warping the entire image of the retina to be approximately horizontal based at least in part on the curve;
   constructing one or more features based on the aligned image of the retina, comprising:
      creating an edge map based on the aligned image;
      constructing at least one (multi-scale) spatial division based on one or more of the aligned image or the edge map, wherein the at least one (multi-scale) spatial division comprises a multi-scale spatial pyramid (MSSP); and
      forming at least one local binary pattern (LBP)-based feature based at least in part on the at least one global representation; and
   classifying the image into a category for each of the one or more macular pathologies, wherein the classifying comprises employing a classifier to determine the category.

* * * * *